United States Patent
Yang et al.

(10) Patent No.: US 10,494,665 B2
(45) Date of Patent: Dec. 3, 2019

(54) TEST KIT AND METHOD FOR TESTING TARGET NUCLEIC ACID IN SAMPLE

(71) Applicants: Huawei Yang, Beijing (CN); Ji Zeng, Beijing (CN)

(72) Inventors: Huawei Yang, Beijing (CN); Ji Zeng, Beijing (CN)

( * ) Notice: Subject to any disclaimer, the term of this patent is extended or adjusted under 35 U.S.C. 154(b) by 121 days.

(21) Appl. No.: 15/504,764

(22) PCT Filed: Aug. 20, 2015

(86) PCT No.: PCT/CN2015/087681
§ 371 (c)(1),
(2) Date: Feb. 17, 2017

(87) PCT Pub. No.: WO2016/026453
PCT Pub. Date: Feb. 25, 2016

(65) Prior Publication Data
US 2017/0268048 A1    Sep. 21, 2017

(30) Foreign Application Priority Data

Aug. 20, 2014   (CN) .......................... 2014 1 0414315
Aug. 20, 2014   (CN) .......................... 2014 1 0414539
Aug. 20, 2014   (CN) .......................... 2014 1 0415012
Aug. 20, 2014   (CN) .......................... 2014 1 0415013

(51) Int. Cl.
| | | |
|---|---|---|
| C12Q 1/68 | (2018.01) | |
| C12Q 1/6832 | (2018.01) | |
| C12Q 1/6825 | (2018.01) | |
| C12Q 1/6834 | (2018.01) | |
| C12Q 1/6816 | (2018.01) | |

(52) U.S. Cl.
CPC ......... *C12Q 1/6832* (2013.01); *C12Q 1/6816* (2013.01); *C12Q 1/6825* (2013.01); *C12Q 1/6834* (2013.01); *C12Y 301/03001* (2013.01)

(58) Field of Classification Search
None
See application file for complete search history.

(56) References Cited

U.S. PATENT DOCUMENTS

| | | | | |
|---|---|---|---|---|
| 3,258,453 A | * | 6/1966 | Chi ............................ | C08F 6/24 526/346 |
| 5,422,242 A | | 6/1995 | Young | |
| 5,702,882 A | * | 12/1997 | Tamura ................ | G01N 33/579 435/13 |
| 5,912,139 A | * | 6/1999 | Iwata ........................ | C12Q 1/32 435/11 |
| 7,361,493 B1 | * | 4/2008 | Hammond ............... | C12N 9/14 435/194 |
| 2001/0010910 A1 | * | 8/2001 | Hyldig-Nielsen ... | C07K 14/003 435/6.12 |
| 2001/0023065 A1 | * | 9/2001 | Lee ......................... | C12Q 1/689 435/6.14 |
| 2002/0115108 A1 | * | 8/2002 | Callen ................... | C12N 9/1252 435/7.1 |
| 2007/0264664 A1 | | 11/2007 | Akhavan-Tafti | |
| 2009/0068164 A1 | * | 3/2009 | Segal .................. | C12N 15/1055 424/94.6 |
| 2009/0304637 A1 | * | 12/2009 | Marchal ............. | A61K 39/0011 424/93.2 |
| 2010/0035260 A1 | * | 2/2010 | Olasagasti ........... | C12Q 1/6869 435/6.16 |
| 2014/0037649 A1 | * | 2/2014 | Brandon ............... | C12Q 1/6883 424/164.1 |
| 2015/0041092 A1 | * | 2/2015 | Hietaniemi .......... | D21H 27/002 162/168.4 |

FOREIGN PATENT DOCUMENTS

| | | |
|---|---|---|
| CN | 101768628 A | 7/2010 |
| CN | 105349620 A | 2/2016 |
| CN | 105648039 A | 6/2016 |
| WO | 2006073472 A2 | 7/2006 |

OTHER PUBLICATIONS

International Search Report and Written Opinion for corresponding International PCT Application No. PCT/CN2015/087681, dated Apr. 7, 2017.

\* cited by examiner

*Primary Examiner* — Bradley L. Sisson
(74) *Attorney, Agent, or Firm* — Workman Nydegger

(57) ABSTRACT

Related to is the field of nucleic acid testing, and in particular, a test kit or a method for testing a target nucleic acid in a sample. The test kit comprises therein a hybridization solution, which contains therein a non-ionic surfactant, a cationic polymer, and a buffer solution having a pH value in the range from 6.5 to 8.5. The test kit can further comprise therein a Tris-HCl color developing solution having a pH value in the range from 9.0 to 10.0 and containing a C8-C18 alkylglucoside. Testing target nucleic acid in a sample using the test kit has the advantages of short time consumption, easy operation, high throughput, and low costs.

8 Claims, 2 Drawing Sheets
Specification includes a Sequence Listing.

TEST KIT AND METHOD FOR TESTING TARGET NUCLEIC ACID IN SAMPLE

CROSS-REFERENCE TO RELATED APPLICATIONS

The present application is a U.S. National Phase Application of PCT/CN2015/087681, entitled "Test Kit and Method for Testing Target Nucleic Acid in Sample" and filed on Aug. 20, 2015; which claims the priority of Chinese patent application CN 201410414315.0, entitled "Method for rapid test of target nucleic acid in sample and use thereof" and filed on Aug. 20, 2014; the priority of Chinese patent application CN 201410415013.5, entitled "Test kit for testing human papillomavirus and use thereof" and filed on Aug. 20, 2014; the priority of Chinese patent application CN 201410414539.1, entitled "Highly specific method for testing target DNA in sample and use thereof" and filed on Aug. 20, 2014; and the priority of Chinese patent application CN 201410415012.0, entitled "Test kit for testing Mycobacterium tuberculosis and drug-resistance gene mutation thereof, and use of the test kit" and filed on Aug. 20, 2014. The entireties of the above applications are incorporated herein by reference.

FIELD OF THE INVENTION

The present disclosure belongs to the field of nucleic acid testing, and in particular, to a test kit or a method for testing a target nucleic acid in a sample.

REFERENCE TO SEQUENCE LISTING SUBMITTED VIA EFS-WEB

This application includes an electronically submitted sequence listing in .txt format. The .txt file contains a sequence listing entitled "21089-1-Sequence Listing.txt" created on Feb. 17, 2017 and is 6 bytes in size. The sequence listing contained in this .txt file is part of the specification and is hereby incorporated by reference herein in its entirety.

BACKGROUND OF THE INVENTION

A fundamental principle of nucleic acid molecular hybridization (hybridization for short), a most basic experimental technique in nucleic acid researches, is to allow, based on denaturation and renaturation properties of nucleic acid molecules, DNA (or RNA) fragments of different origins to form hybrid double-stranded molecules in accordance with a base complementary relationship. Hybrid double strands can be formed either by DNA strands or alternatively by RNA and DNA strands. Currently, hybridization has become one of the most frequently used nonradioactive genetic diagnosis technologies in modern molecular biology laboratories. It can be used to test not only gene mutations that would cause canceration or various hereditary diseases (such as thalassemia), but also bacteria, viruses, parasites, and the like that would cause infectious diseases.

Based on different environments in which reactions are performed, hybridization can be divided into solid-phase hybridization and liquid-phase hybridization. And according to different utilization purposes in laboratories, hybridization can include dot (or slot) hybridization, Southern blot hybridization, Northern blot hybridization, cell in situ hybridization, chromosome in situ hybridization, etc.

In solid-phase hybridization, of two nucleic acid strands to participate in a reaction, one is first immobilized onto a solid support, and the other is free in a solution. Depending on different positions of sample molecules to be detected, solid-phase hybridization can be divided into forward hybridization (in which case the sample molecules to be detected are immobilized on a film, while a detecting probe is placed in the solution), and reverse hybridization (in which case the sample molecules to be detected are placed in the solution, while the detecting probe is immobilized on the film). By reverse hybridization, it means to hybridize a labeled sample nucleic acid with an unlabeled and immobilized nucleic acid probe. The advantage of reverse hybridization lies in that multiple nucleic acids in a sample can be simultaneously detected in one hybridization reaction.

Existing reverse hybridization technologies are performed in complicated operations, involving numerous reaction solutions and steps. In particular, when multiple samples are to be detected, the operating time will be remarkably prolonged and errors would easily occur. For example, CN 101768628A discloses a method for detecting nucleic acid point mutations, and specifically discloses a method for detecting nucleic acid point mutations through reverse hybridization performed on a PCR product with an oligonucleotide probe. However, to perform such a method, it is necessary to test a hybridization result with the aid of an expensive fluorescence detection device. This not only involves tedious operations, but is of high costs as well.

As a result, there is an urgent need of a product and a method for rapid detection of a target nucleic acid in a sample.

SUMMARY OF THE INVENTION

Out of such considerations, the inventors of the present disclosure have conducted researches, to solve problems exposed in related prior arts. The present disclosure aims to provide a test kit for rapid detection of a target nucleic acid in a sample, characterized by short time consumption, easy operation, high throughput, and low costs. The present disclosure further aims to provide a method for detecting a target nucleic acid in a sample.

Therefore, the present disclosure provides a test kit for detecting a target nucleic acid in a sample. The test kit comprises therein a hybridization solution, which contains therein a non-ionic surfactant, a cationic polymer, and a buffer solution having a pH value in the range from 6.5 to 8.5. Furthermore, 3×SSC buffer solution having a pH value in the range from 6.5 to 8.5 or a phosphate buffer solution having a pH value in the range from 6.5 to 8.5 can be selected. The buffer solution is preferably 3×SSC buffer solution having a pH value in the range from 6.5 to 7.2, and more preferably 3×SSC buffer solution having a pH value of 7.0.

In the present disclosure, the hybridization solution further contains a cationic polymer, besides base components, i.e., the buffer solution having a pH value in the range from 6.5 to 8.5, and a certain amount of the non-ionic surfactant. In their researches, the inventors have discovered that electrostatic adsorption can be generated between a cationic polymer and a biotin-labeled target nucleic acid (for example, biotin-labeled target nucleic acid molecules obtained through PCR amplification), such that single-stranded nucleic acid molecules (having many negative electric charges) can be charged with positive electric charges, and can thus be simultaneously adsorbed on a surface of a solid support during hybridization of nucleic acid molecules. As alkaline phosphatase labeled-streptavidin has positive electric charges also, alkaline phosphatase can be prevented from being non-specifically adsorbed on the surface of the solid support. In addition, the cationic polymer enables alkaline phosphatase labeled-streptavidin to form a homogeneous suspension in the hybridization solution, such that after a hybridization reaction, alkaline phosphatase labeled on a nucleic acid conjugate maintains in an active state. Hence, the equilibrium shift of alkaline phosphatase conformation can move toward a natural state.

The test kit of the present disclosure can be used not only for DNA detection, but also for RNA detection, wherein during RNA detection, operation should be performed in an RNase-free environment.

Moreover, the test kit of the present disclosure can be used not only in alkaline phosphatase color development system, but also in a chemiluminescence system.

In one specific embodiment, the cationic polymer is at least one selected from a group consisting of cationic polyacrylamide, polylysine, and polyaluminium chloride.

In one specific embodiment, the non-ionic surfactant contained in the hybridization solution can be a ploysorbate and/or a polyethylene glycol octylphenyl ether, including non-ionic surfactants sold under the trademark TWEEN (Polysorbate) and/or TRITON (Octoxynol).

In one specific embodiment, in the hybridization solution, the ratio of the weight of the cationic polymer to the volume of the non-ionic surfactant is (1-50):(1-200), preferably (1-4):(1-20).

In the test kit of the present disclosure, as the inventors have discovered through extensive experiments and creative labor, any changes in acid, alkali, salt ions, or temperature may alter or even completely neutralize the activity of alkaline phosphatase. In order to achieve the purpose of direct addition of alkaline phosphatase labeled-streptavidin in the hybridization solution of the present disclosure, it is extremely important to select components of the hybridization solution. In the test kit of the present disclosure, zinc ions, magnesium ions, protein, and non-ionic surfactant are added in the hybridization solution, which not only improves hybridization efficiency of nucleic acids, but also prevents denaturation of alkaline phosphatase labeled-streptavidin in the hybridization solution due to adsorption, and polymerization denaturation of alkaline phosphatase labeled-streptavidin molecules caused by interaction therebetween.

In addition, the protein and non-ionic surfactant in the hybridization solution can further generate a synergistic effect, and be bound together to the surface of the solid support via Van der Waals' force, thereby effectively preventing non-specific adsorption of unreacted alkaline phosphatase labeled-streptavidin and/or biotin-labeled target nucleic acid on the surface of the solid support. This plays a rather favorable sealing effect. As a result, a pre-hybridization step can be cancelled in method of the present disclosure before the hybridization reaction.

Thus, in detection of the target nucleic acid, on the one hand, alkaline phosphatase labeled-streptavidin can be sufficiently bound to the biotin-labeled target nucleic acid or biotin-labeled nucleic acid probe, so as to form a conjugate of an alkaline phosphatase-labeled nucleic acid hybrid and eliminate a separate step of ELISA (enzyme linked immunosorbent assey) and a plurality of other steps after the hybridization reaction in conventional reverse molecular hybridization. This can shorten the reaction time of nucleic acid hybridization. On the other hand, the efficiency of nucleic acid hybridization can be promoted.

Therefore, in one specific embodiment, the hybridization solution further contains zinc ions and/or magnesium ions.

In the hybridization solution, the weight ratio of the zinc ions to the cationic polymer is preferably (13-1300):(20-1000), more preferably (13-130):(20-80); and the weight ratio of the magnesium ions to the cationic polymer is preferably (6-600):(25-1250), more preferably (12-120):(25-100).

In one specific embodiment, the zinc ions can be selected from soluble salts containing zinc ions. Therefore, examples of the soluble salts containing zinc ions of the present disclosure include zinc sulfate, zinc chloride, and various other salts from which zinc ions can be dissociated in a solution.

In one specific embodiment, the magnesium ions can be selected from soluble salts containing magnesium ions. Therefore, examples of the soluble salts containing magnesium ions of the present disclosure include magnesium sulfate, magnesium acetate, magnesium chloride, and various other salts from which magnesium ions can be dissociated in a solution.

In one specific embodiment, the hybridization solution further contains therein alkaline phosphatase labeled-streptavidin, wherein the weight ratio of the alkaline phosphatase labeled-streptavidin to the cationic polymer is preferably (1-40):(2000-100,000), more preferably (1-15):(5000-20,000), and further preferably (5-12):(5000-20,000).

In one specific embodiment, the hybridization solution further contains therein a protein, which is at least one selected from a group consisting of albumin, casein, and gelatin. The weight ratio of the protein to the cationic polymer is preferably (10-1000): (1-50), more preferably (20-100):(1-4).

In one specific embodiment, the hybridization solution does not contain therein ethylenediamine tetraaetate, inorganic phosphate, or ethanolamine.

In the test kit of the present disclosure, the hybridization solution can further contain therein a hybridization accelerator, which is essentially known by those skilled in the art. Examples that can be used as the hybridization accelerator of the present disclosure include but are not limited to dextran sulfate, polyethylene glycol, phenol, and guanidine thiocynanate.

In the test kit of the present disclosure, the hybridization solution can further contain therein other components. Examples of other components contained in the hybridization solution that can be listed include but are not limited to sodium chloride, hybridization buffer solutions, Denhardt's solutions, sodium dodcyl sarcosinate, and sodium dodecyl sulfonate. Examples of the hybridization buffer solution that can be used in the present disclosure include but are not limited to citric acid-sodium citrate buffer solution and Tris-hydrochloric acid buffer solution.

In one specific embodiment, the test kit further contains therein a Tris-HCl color developing solution having a pH value in the range from 9.0 to 10.0.

In one specific embodiment, the color developing solution further contains therein a $C_8$-$C_{18}$ alkylglucoside, preferably a $C_9$-$C_{13}$ alkylglucoside. On the condition that an enzyme-catalyzed reaction of a substrate is non-affected, the above alkylglucoside can be added into the color developing solution, to enable the color developing solution to acquire a significant washing effect. Thus, a conventional washing step can be eliminated before color development, thereby largely shortening necessary time for detection of the target nucleic acid.

In one specific embodiment, the weight ratio of the alkylglucoside to Tris is (1-50):121, preferably (5-10):121.

In one specific embodiment, the pH value of the color developing solution is in the range from 9.3 to 9.7, preferably being 9.5. Through extensive experiments and creative labor, the inventors of the present disclosure have discovered that, in the test kit of the present disclosure, a synergistic effect can be generated during color development especially between Tris-HCl buffer solution and alkylglucoside, so as to wash the surface of the solid support, and remove substances that are non-specifically adsorbed on the surface of the solid support. As a result, the substrate can generate a color product for color development through an enzymatic reaction directly in the color developing solution without a separate film-washing step after hybridization. Hence, it is particularly preferred that the color developing solution is Tris-HCl buffer solution having a pH value of 9.5.

In one specific embodiment, the test kit comprises therein a pretreatment solution and a preliminary treatment solution. The pretreatment solution contains a Tris-HCl buffer solution having a pH value in the range from 7.0 to 8.0, NaCl, a sealant, and a non-ionic surfactant. The preliminary treatment solution contains NaCl and a buffer solution having a pH value in the range from 7.0 to 9.0, which is selected from a group consisting of barbital sodium-hydrochloric acid buffer solution, Tris-HCl buffer solution, glycine-sodium hydroxide buffer solution, and boric acid-borax buffer solution.

The pretreatment solution and preliminary treatment solution contained in the test kit of the present disclosure can be used to cooperatively treat the surface of the solid support before and after the one-step reaction, thereby improving hybridization specificity of nucleic acid molecules on the surface of the solid support. This can effectively avoid a false positive result.

The inventors of the present disclosure have found, through extensive experiments and creative labor, in the test kit of the present disclosure, the pH value of the pretreatment solution influences electrical properties of a variety of components contained therein. When the pH value of the pretreatment solution is in the range from 7.0 to 8.0, the sealant is not charged, such that only a small resistance can be generated in the interaction between an anionic dispersant and the sealant. As a result, a favorable dispersing effect can be produced by the sealant in the pretreatment solution. When there is anionic polyacrylamide, the sealant can be more readily adsorbed onto a solid/liquid interface, and the adsorption force between the sealant and the solid support can be stronger.

In one specific embodiment, the sealant contained in the pretreatment solution is casein and/or bovine serum albumin, and the non-ionic surfactant contained therein is TWEEN (Polysorbate) and/or TRITON (Octoxynol). In the pretreatment solution, the weight ratio of the sealant to Tris is (100-500):121, preferably (200-400):121; and the weight ratio of the non-ionic surfactant to Tris is (5-100):121, preferably (5-20):121.

In one specific embodiment, the non-ionic surfactant can be selected from those sold under the trade name TWEEN (Polysorbate), and can be at least one selected from a group consisting of TWEEN-20 (Polysorbate-20), TWEEN-21 (Polysorbate-21), TWEEN-40 (Polysorbate-40), TWEEN-60 (Polysorbate-60), TWEEN-61 (Polysorbate-61), TWEEN-80 (Polysorbate-80), TWEEN-81 (Polysorbate-81), and TWEEN-85 (Polysorbate-85), wherein TWEEN-20 (Polysorbate-20) is particularly preferred.

In one specific embodiment, the non-ionic surfactant can be selected from those sold under the trade name TRITON (Octoxynol), and can be TRITON X-100 (Octoxynol-9), TRITON X-114 (Octoxynol-7), or TRITON X-200 (Sodium octoxynol sulfonate), wherein TRITON X-100 (Octoxynol-9) is particularly preferred.

In one specific embodiment, the pretreatment solution further contains therein an anionic dispersant and/or anionic polyacrylamide.

The inventors of the present disclosure have discovered, through extensive experiments and creative labor, in the test kit of the present disclosure, the anionic dispersant and/or anionic polyacrylamide added in the pretreatment solution can be compounded with the sealant and the non-ionic surfactant, to effectively improve adsorption effects of the sealant and the non-ionic surfactant on a hydrophobic interface, thereby largely improving the specificity of the test results.

In the test kit of the present disclosure, the anionic dispersant can generate a sufficient energy barrier against the sealant, thus ensuring stable dispersion of the sealant in the pretreatment solution. The anionic dispersant and the sealant produce an adsorption effect in the pretreatment solution, which can reduce mechanical work necessary for disaggregation of the sealant. The anionic dispersant is compounded with the non-ionic surfactant, to further improve the sealing effect of the non-ionic surfactant. The anionic polyacrylamide can decrease the Stern potential on the solid/liquid interface, and decrease an electrical energy barrier, thus facilitating effective adsorption of the sealant and the non-ionic surfactant, which are dispersed in the pretreatment solution, to the surface of the solid support. As the hydrophilic group of polyacrylamide can be preferentially adsorbed onto the surface of the solid support, the hydrophobic group thereof points to the aqueous phase, such that the tension on the solid/liquid interface becomes larger, and the water repellency on the surface of the solid support increases. As a result, when the sealant is in contact with the surface of the solid support, hydrophobic chains extending into the aqueous phase interact with each other to allow the sealant to flocculate in the pretreatment solution and to be effectively adsorbed onto the surface of the solid support.

In one preferred embodiment of the present disclosure, the anionic dispersant is preferably sodium lignosulphonate, which is a natural polymer and has such a strong dispersion that it can be adsorbed on the surface of solid particles. Existence of a variety of active groups in the structure of sodium lignosulphonate enables it to form hydrogen bonds with the sealant.

In one further preferred embodiment of the present disclosure, the weight ratio of the anionic dispersant to Tris is preferably (5-20):121, more preferably (10-15):121.

In one specific embodiment, the weight ratio of the anionic polyacrylamide to Tris is (2-50):121, preferably (10-30):121.

In one specific embodiment, the test kit further comprises therein an aftertreatment solution, which contains a buffer solution having a pH value in the range from 9.0 to 10.0.

The inventors of the present disclosure have discovered, through extensive experiments and creative labor, using the aftertreatment solution to wash the surface of the solid support after the above reaction can achieve a better effect in subsequent color development. On the one hand, the aftertreatment solution can wash biotin-labeled nucleic acid probe molecules that are not hybridized or non-specifically hybridized with the target nucleic acid off the surface of the solid support, and retain specific hybrids on the surface of the solid support. On the other hand, alkaline phosphatase can still be maintained active after the solid support is washed with the aftertreatment solution. This can ensure subsequent color development efficiency, so as to achieve a better color difference effect.

In one specific embodiment, the aftertreatment solution further contains therein magnesium ions, e.g., magnesium chloride and/or magnesium sulfate, and/or a C8-C18 alkylglucoside, preferably magnesium ions and/or a C9-C13 alkylglucoside. It should be noted herein that the aftertreatment solution and the color developing solution can both be added with the alkylglucoside. Generally, however, it will be sufficient to add the alkylglucoside in either one of the above two solutions used. That is, in one operation, it is necessary to use the color developing solution. In case the aftertreatment solution is not used, the alkylglucoside can be added into the color developing solution. When the aftertreatment solution is used also, it is preferred that the alkylglucoside should be added into the aftertreatment solution, although it can still be added into the color developing solution instead.

In one specific embodiment, the weight ratio of the alkylglucoside to Tris in the aftertreatment solution is (10-500):121, preferably (50-200):121.

In one specific embodiment, the test kit further comprises at least one optionally selected from a group consisting of alkaline phosphatase labeled-streptavidin, a solid support immobilized with at least one nucleic acid probe for detecting a target nucleic acid or a solid support immobilized with at least one target nucleic acid, a PCR reagent, a color developing substrate solution, a positive control sample, and a negative control sample. The color developing substrate solution can be aqueous solution of nitro blue tetrazolium (NBT) or aqueous solution of 5-bromo-4-chloro-3-indolyl-phosphoric acid (BCIP).

In one specific embodiment, the target nucleic acid can be extracted from prokaryotes of the Bacteriophyt (including actinomycetes), the Cyanophyta, the Prochlorophyta, the *Rickettsia, mycoplasma*, and *chlamydia*, etc, fungi of the Myxomycota and the Eumycophyta, etc, plants of the Euglenophyta, the Chlorophyta, the Charophyta, the Chrysophyta, the Pyrrophyta, the Phaeophyta, the Rhodophyta, the Cyanophyta, the Bacteriophyt, the Myxomycophyta, the Eumycophyta, the Lichens, the Bryophyta, the Pteridophyta, the Gymnospermae, and the Angiospermae, etc, animals of the Protozoa, the Mesozoa, the Porifera, the Placo-zoa, the Cnidaria, the Ctenophora, the Platyhelminthes, the Nemertea, the Gnathostomulida, the Rotifera, the Gastro-tricha, the Kinorhyncha, the Nematoda, the Nematomorpha, the Priapula, the Acanthocephala, the Entoprocta, the Loricifera, the Annelida, the Echiura, the Sipuncula, the Pogonophora, the Vestimentifera, the Tardigrada, the Onychophora, the Arthropoda, the Mollusca, the Brachiopoda, the Ectoprocta, the Phoronida, the Chaetognatha, the Echinoderma-ta, the Hemichordata, and the Chordata, etc, and protozoa.

In one specific embodiment, the substrate solution can be selected from but is not limited to the group consisting of aqueous solution of NBT, aqueous solution of BCIP, fast red solution, and naphthol ASMX solution. Under the catalysis of alkaline phosphatase, BCIP will be hydrolyzed to produce a strong reactive product that will react with NBT to form insoluble dark blue to blue-violet NBT-formazan.

In one specific embodiment, the solid support can be selected from a group consisting of nylon film, nitrocellulose membrane, and polypropylene film, wherein nylon film and nitrocellulose membrane are preferred, and nitrocellulose membrane is particularly preferred.

In the test kit of the present disclosure, the target nucleic acid can be immobilized on the surface of the solid support through non-covalent or covalent bonds. Non-covalent bond immobilization of the target nucleic acid can be achieved through a hydrophobic effect or through attraction between negative charges of the phosphate anions in the target nucleic acid and positive charges on the surface of the solid support. Covalent bond immobilization of the target nucleic acid on the surface of the solid support can be achieved through covalent bonds, such as amide bonds, ester bonds, and ether bonds.

In one specific embodiment, the nucleic acid probe can be selected from oligonucleiotide probes each having 15-40, preferably 16-25 bases.

According to the test kit of the present disclosure, a proper length of the nucleic acid probe and a proper content of GC contained therein can be selected to reduce the temperature necessary for hybridization between the nucleic acid probe and the biotin-labeled target nucleic acid. As a result, the hybridization and ELISA can be performed in one and the same reaction system. The inventors of the present disclosure have discovered, through extensive experiments, the nucleic acid probe can be properly selected from oligonucleotide probes each having 15-40, preferably 16-25, bases. Under such circumstances, the temperature of the hybridization can be in the range from 37 to 42° C. It is particularly preferred that the nucleic acid probe should comprise 16, 17, 18, 19, 20, 21, 22, 23, 24, and 25 bases.

According to the test kit of the present disclosure, the length of the nucleic acid probe should be selected with the following considerations. If the nucleic acid probe is too short, the sensitivity of probe hybridization will be significantly reduced, although the specificity thereof can be improved; while if the nucleic acid probe is too long, although sensitivity of probe hybridization will be further improved, the specificity thereof will be significantly decreased, such that a variety of similar human papillomavirus (HPV) genotypes, for example, will be especially difficult to differentiate from each other. The specificity of probe hybridization of an excessively long nucleic acid probe cannot be improved through increase of the hybridization temperature either, because too high a temperature will deactivate alkaline phosphatase labeled-streptavidin in the hybridization system. With considerations of both the above various factors, and influences of the GC content of the probe on a Tm value of the hybridization, an oligonucleotide probe having 16-25 bases is preferred.

According to one specific embodiment of the present disclosure, the biotin-labeled nucleic acid probe is an oligonucleotide probe having a biotin-labeled 5' end.

The above nucleic acid probe and the target nucleic acid detected thereby can be either labeled or unlabeled with biotin as per specific conditions. For example, when the nucleic acid probe is immobilized on the solid support, while the target nucleic acid is placed in the hybridization solution, the nucleic acid probe will be unnecessary to be biotin-labeled, while the target nucleic acid should be biotin-labeled. However, when the nucleic acid probe is placed in the hybridization solution, while the target nucleic acid is immobilized on the solid support, the nucleic acid probe should then be biotin-labeled, and the target nucleic acid will be unnecessary to be labeled with biotin.

The test kit of the present disclosure can be used for detecting HPV. As is known in the prior art, HPV encodes 6-8 early proteins E and 2 late proteins L. Genes L1 and L2 respectively encode major capsid protein L1 and secondary capsid protein L2, which constitute capsid proteins of the virus. Protein L1, with a rather conservative sequence, is a main species-specific HPV antigen. Gene L1, corresponding to protein L1, is 1.5 kb in length. In accordance with polymorphism and conservativeness of gene L1, HPV can be divided into multiple genotypes. Therefore, in one specific embodiment, nucleic acid probes can be designed to detect HPV.

In the test kit of the present disclosure, the inventors have selected clinically most important 13 HPV genotypes (16, 18, 31, 33, 35, 39, 45, 51, 52, 56, 58, 59, and 68) as detection objects. Through extensive experiments and creative labor, and researches into numerous HPV nucleic acid sequences, 38 oligonucleotide probes of high specificity and sensitivity are designed for the 13 HPV genotypes, respectively. Because the nucleic acid sequences of genes L1 of different HPV genotypes are rather similar to each other, the inventors of the present disclosure have conducted extensive targeted experiments on primarily selected oligonucleotide probes for verification, and screened out useful and highly specific probes.

The nucleic acid probe is at least one selected from a group consisting of:

an oligonucleotide probe, the sequence of which is shown in SEQ ID NO: 13, for detecting *Mycobacterium tuberculosis*;

an oligonucleotide probe, the sequence of which is shown in SEQ ID NO: 14, for detecting *Mycobacterium avium*;

an oligonucleotide probe, the sequence of which is shown in SEQ ID NO: 15, for detecting a *Mycobacterium* intracellular;

an oligonucleotide probe, the sequence of which is shown in SEQ ID NO: 16, for detecting *Mycobacterium fortuitum*;

an oligonucleotide probe, the sequence of which is shown in SEQ ID NO: 17, for detecting *Mycobacterium abscessus*;

an oligonucleotide probe, the sequence of which is shown in SEQ ID NO: 18, for detecting *Mycobacterium kansasii*;

an oligonucleotide probe, the sequence of which is shown in SEQ ID NO: 19, for detecting T533C wild type of the rpoB gene of *Mycobacterium tuberculosis*;

an oligonucleotide probe, the sequence of which is shown in SEQ ID NO: 2, for detecting T533C mutant of the rpoB gene of *Mycobacterium tuberculosis*;

an oligonucleotide probe, the sequence of which is shown in SEQ ID NO: 20, for detecting C531T wild type of the rpoB gene of *Mycobacterium tuberculosis*;

an oligonucleotide probe, the sequence of which is shown in SEQ ID NO: 21, for detecting C531T mutant of the rpoB gene of *Mycobacterium tuberculosis*;

an oligonucleotide probe, the sequence of which is shown in SEQ ID NO: 22, for detecting 526 wild type of the rpoB gene of *Mycobacterium tuberculosis*;

an oligonucleotide probe, the sequence of which is shown in SEQ ID NO: 23, for detecting C526G mutant of the rpoB gene of *Mycobacterium tuberculosis*;

an oligonucleotide probe, the sequence of which is shown in SEQ ID NO: 24, for detecting C526T mutant of the rpoB gene of *Mycobacterium tuberculosis*;

an oligonucleotide probe, the sequence of which is shown in SEQ ID NO: 25, for detecting A526T mutant of the rpoB gene of *Mycobacterium tuberculosis*;

an oligonucleotide probe, the sequence of which is shown in SEQ ID NO: 26, for detecting A526G mutant of the rpoB gene of *Mycobacterium tuberculosis*;

an oligonucleotide probe, the sequence of which is shown in SEQ ID NO: 27, for detecting A516T wild type of the rpoB gene of *Mycobacterium tuberculosis*;

an oligonucleotide probe, the sequence of which is shown in SEQ ID NO: 28, for detecting A516T mutant of the rpoB gene of *Mycobacterium tuberculosis*;

an oligonucleotide probe, the sequence of which is shown in SEQ ID NO: 29, for detecting T511C wild type of the rpoB gene of *Mycobacterium tuberculosis*;

an oligonucleotide probe, the sequence of which is shown in SEQ ID NO: 30, for detecting T511C mutant of the rpoB gene of *Mycobacterium tuberculosis*;

a nucleic acid probe, the nucleotide sequence of which is shown in SEQ ID NO: 35, for detecting HPV genotype 16;

a nucleic acid probe, the nucleotide sequence of which is shown in SEQ ID NO: 36, for detecting HPV genotype 18;

a nucleic acid probe, the nucleotide sequence of which is shown in SEQ ID NO: 37, for detecting HPV genotype 31;

a nucleic acid probe, the nucleotide sequence of which is shown in SEQ ID NO: 38, for detecting HPV genotype 33;

a nucleic acid probe, the nucleotide sequence of which is shown in SEQ ID NO: 39, for detecting HPV genotype 35;

a nucleic acid probe, the nucleotide sequence of which is shown in SEQ ID NO: 40, for detecting HPV genotype 39;

a nucleic acid probe, the nucleotide sequence of which is shown in SEQ ID NO: 41, for detecting HPV genotype 45;

a nucleic acid probe, the nucleotide sequence of which is shown in SEQ ID NO: 42, for detecting HPV genotype 51;

a nucleic acid probe, the nucleotide sequence of which is shown in SEQ ID NO: 43, for detecting HPV genotype 52;

a nucleic acid probe, the nucleotide sequence of which is shown in SEQ ID NO: 44, for detecting HPV genotype 56;

a nucleic acid probe, the nucleotide sequence of which is shown in SEQ ID NO: 45, for detecting HPV genotype 58;

a nucleic acid probe, the nucleotide sequence of which is shown in SEQ ID NO: 46, for detecting HPV genotype 59; and a nucleic acid probe, the nucleotide sequence of which is shown in SEQ ID NO: 47, for detecting HPV genotype 68.

In the test kit of the present disclosure, considering that some HPV genotypes, such as HPV 45, HPV 52, and HPV 59, include commonly seen gene subtypes, the inventors have, in light of such genotypes, designed degenerate nucleic acid probes, which can simultaneously detect various gene subtypes of these genotypes without any leak detection. With comprehensive considerations of the specificity, sensitivity, and coverage over different gene subtypes of some genotypes, the inventors have eventually selected these preferred nucleic acid probes, the sequences of which are shown in SEQ ID NOs: 35-47.

According to one specific embodiment of the present disclosure, the test kit of the present disclosure can further comprise therein a positive control sample and a negative control sample, wherein a whole genome plasmid of HPV genotype 16 can be selected as the positive control sample and Salmon sperm DNA can be selected as the negative control sample.

According to one specific embodiment of the present disclosure, the target nucleic acid can be extracted from a cervical exfoliated cell sample of a subject, with the test kit of the present disclosure through a conventional DNA extraction procedure, or with a commercially available DNA extraction kit.

According to one specific embodiment of the present disclosure, the test kit of the present disclosure can be allowed to identify high-risk HPV types without having to indicate what specific high-risk types exist in the sample.

High-risk types (those found in high-grade squamous intraepithelial lesion (SIL) or carcinoma in situ) include but are not limited to HPV types 16, 18, 31, 33, 35, 39, 45, 51, 52, 56, 58, 59, 66, and 68.

Low-risk types (those substantially found on low-grade SIL) include but are not limited to HPV types 6, 11, 34, 40, 42, 43, 44, 53, 70, and 74.

The test kit of the present disclosure can be further used in detection of mycobacteria. The probes for detecting mycobacteria can be designed in accordance with the 16S rDNA gene sequence of the mycobacteria. The 16S rDNA gene, a most useful and most commonly used molecular clock, exists in all organisms, and shows fine clock properties in evolution, and high conservativeness in both structure and function thereof, such that it is known as "bacterial fossil." The 16S rDNA gene, of moderate size and about 1.5 kb in base length, can be conveniently used in PCR amplification and sequencing, and is a standard procedure for phylogenetic relationship classification. The structure of the 16S rDNA gene can comprise a variable region and a constant region. The sequences of the constant regions substantially keep conservative in different bacteria, while the sequences of variable regions vary in different bacteria. Therefore, the 16S rDNA gene can be amplified through design of a primer according to the sequence of the constant region, and different sequences in the variable regions can be referred to, to design specific probes and to classify different bacteria. The *Mycobacterium* probes designed in the present disclosure are capable of specifically identifying *Mycobacterium tuberculosis* (including human *Mycobacterium tuberculosis*, *Mycobacterium bovis*, and *Mycobacterium africanus*, which have highly consistent gene sequences and pathogenicity, and therefore are unnecessary to be further divided), *Mycobacterium avium* complex, *Mycobacterium intracellulare*, *Mycobacterium fortuitum*, *Mycobacterium abscessus*, and *Mycobacterium kansasii*, without any occurrence of cross reactions with other bacterial species or other mycobacterial species.

To detect a mutation in the rpoB gene of *Mycobacterium tuberculosis*, two probes, i.e., a wild-type (non-mutant) probe and a mutant probe are designed for each base mutation. For example, when no mutation occurs at codon 531 in the rpoB gene as detected, the probe for detecting 531 wild-type will be positive, and its corresponding probe for detecting C531T mutant will be negative; while when a C→T mutation occurs at codon 531 in the rpoB gene as detected, the probe for detecting 531 wild-type will be negative, and the probe for detecting C531T mutant will be positive. Satisfactory identification of occurrence of different single base mutations can thus be possible. Meanwhile, in order to overcome the defect of insensitive signals in detection of single base mutations with a conventional probe, specific design has been provided in the present disclosure, i.e., the length of the oligonucleotide probe has been significantly increased on the basis of introduction of artificial missense mutations, thereby substantially improving hybridization signals of the nucleic acid probes on condition that a high degree of specificity of these probes is maintained.

In one specific embodiment, the nucleic acid probes further include a positive control probe, the sequence of which is shown in SEQ ID NO: 3. The positive control probe of the present disclosure, which can be extracted from human actin genes, is capable of not only achieving highly specific detection of existence of a human genome in a sample, but also controlling extraction quality of a nucleic acid from a clinical sample and normal performance of detection reactions.

In one specific embodiment, the nucleic acid probes further include a negative control probe, the sequence of which is shown in SEQ ID NO: 4. The negative control probe of the present disclosure can be a random sequence generated by primer design software. Such a random sequence, dissimilar to any biological nucleic acid, can play a very favorable negative control effect, and control specificity of the detection reactions.

In one specific embodiment, the PCR reagent comprises a first primer set, which includes a primer pair used for amplification of the 16S rDNA gene and a primer pair used for amplification of the rpoB gene, wherein the sequence of an upstream primer for amplification of the 16S rDNA gene is shown in SEQ ID NO: 31;

the sequence of a downstream primer for amplification of the 16S rDNA gene is shown in SEQ ID NO: 32;

the sequence of an upstream primer for amplification of the rpoB gene is shown in SEQ ID NO: 33; and the sequence of a downstream primer for amplification of the rpoB gene is shown in SEQ ID NO: 34.

The upstream primer of each of the primer pairs has a biotin-labeled 5' end.

In one specific embodiment, the PCR reagent comprises a primer pair used for amplifying the actin gene as the positive control, wherein an upstream primer used for amplifying the actin gene has a sequence as shown in SEQ ID NO: 7 and a biotin-labeled 5' end, and a downstream primer used for amplifying the actin gene has a sequence shown in SEQ ID NO: 8.

According to the test kit of the present disclosure, multiple PCR primer pairs are used to perform PCR amplification and biotin labeling on the target nucleic acid. Among the multiple primer pairs, one primer pair is used for amplifying the 16S rDNA gene. A product thereof is to be detected with an oligonucleotide probe, which is immobilized on the surface of the solid support and has a nucleotide sequence selected from SEQ ID NOs: 11-28. *Mycobacterium tuberculosis*, *Mycobacterium avium* complex, *Mycobacterium intracellulare*, *mycobacterium fortuitum*, *Mycobacterium abscessus*, and *Mycobacterium kansasii* can be identified thereby. Another primer pair is used for amplifying the rpoB gene. A product thereof is to be detected with an oligonucleotide probe, which is immobilized on the surface of the solid support and has a nucleic acid sequence selected from SEQ ID NOs: 29-54. Mutations of C531T, C526G, T533C, C526T, A526T, A526G, A516T, and T511C can be detected thereby. In addition, the test kit of the present disclosure further comprises a positive control primer pair, for quality control of the PCR reaction system. Hence, while being used to identify *Mycobacterium tuberculosis*, the test kit of the present disclosure can also detect whether the *Mycobacterium tuberculosis* is sensitive or resistant to rifampin.

In order to improve the specificity of the nucleic acid probe in the test kit used for detecting *Mycobacterium tuberculosis* according to the present disclosure, while the sequence of the nucleic acid probe is being designed, one artificial missense mutant base is introduced into each nucleic acid probe used for detecting a gene mutation. When a conventional procedure is used to detect a single base mutation, in order to identify a single base difference, it is necessary to shorten the sequence of the nucleic acid probe into 15-16 bases. This leads to the defects of very weak hybridization signals of the nucleic acid probe and cross-reaction that still occurs easily due to mismatch of single bases. In order to solve such a problem, in the present disclosure, one artificial missense mutation is introduced into the sequence of a nucleic acid probe used for detecting a gene mutation at a codon adjacent to an end of the nucleic acid probe, and meanwhile, the nucleic acid probe is increased to 18-20 bases in length, thereby significantly improving hybridization efficiency of the nucleic acid probe. Therefore, when the test kit of the present disclosure is used for detecting a wild-type rpoB gene, hybridization will not occur between the nucleic acid probe and the target nucleic acid, so long as there are two mismatched base pairs between the sequence of the nucleic acid probe and the sequence of the target nucleic acid. In the case of the wild-type probe and the target nucleic acid, however, although there is also one mismatched base pair, as the base involved in the nucleic acid probe is adjacent to an end thereof, effective hybridization will still occur between the wild-type probe and the target nucleic acid. When the test kit of the present disclosure is used for detecting a mutant rpoB gene, hybridization will not occur between the wild-type probe and the target nucleic acid as there are two mismatched base pairs between the sequences thereof. However, although there is also one mismatched base pair between the mutant probe and the target nucleic acid, the base involved in the nucleic acid probe is adjacent to an end thereof also. Effective hybridization will therefore still occur between the mutant probe and the target nucleic acid.

In one specific embodiment, the PCR reagent further comprises an enhanced primer pair used for enhancing the PCR amplification efficiency of the primer pair, wherein an upstream primer of the enhanced primer pair has a sequence shown in SEQ ID NO: 48 and a biotin-labeled 5' end, and a downstream primer of the enhanced primer pair a sequence shown in SEQ ID NO: 49.

In the test kit of the present disclosure, the sequence of the enhanced primer pair is meanwhile a part of the sequence of the first primer set or the second primer set, and can be used to improve the PCR amplification efficiency of the two primer sets.

In one specific embodiment, when the enhanced primer pair and the first primer set are used together as mixed primers, the PCR amplification efficiency of the primer pair used for amplifying the rpoB gene can be enhanced.

In one specific embodiment, when the enhanced primer pair and the second primer set are used together as mixed primers, the PCR amplification efficiency of the primer pair used for amplifying the 16S rDNA gene and that for amplifying the rpoB gene can be simultaneously enhanced.

In the test kit of the present disclosure, the working principle of the enhanced primer pair is as follows. Besides the enhanced primer pair added into the PCR reaction system, a sequence for enhancing a primer is also ligated to the 5' end of the primer pair used for amplifying the rpoB gene and/or the 5' end of the primer pair used for amplifying the 16S rDNA gene. Thus, fragments of the rpoB gene or/and the 16S rDNA gene are amplified at the beginning of the amplification of the sample. In this case, an enhanced primer sequence is introduced into these fragments. The enhanced primer pair (at a high concentration) then starts to work, and efficiently amplifies the fragments of the rpoB gene or/and the 16S rDNA gene. Therefore, the amplification efficiency of the rpoB gene or/and the 16S rDNA gene is significantly increased, thereby significantly improving the detection sensitivity of rpoB gene mutations.

In the test kit of the present disclosure, a sequence for encoding a 16S rRNA gene is used as the basis for bacterial classification, and six pathogenic mycobacteria of highest isolating rates can be identified as a test kit detection index by a single detection experiment. They are *Mycobacterium tuberculosis*, *Mycobacterium avium* complex, *Mycobacterium intracellulare*, *Mycobacterium fortuitum*, *Mycobacterium abscessus*, and *Mycobacterium kansasii*. In addition, the test kit of the present disclosure can be used to detect 8-10 gene mutations of the rpoB gene at amino acid positions 531, 526, 516, 533, 511, and 513 (with a total clinical coverage of higher than 90%), so as to reflect the resistance of *Mycobacterium tuberculosis* to rifampicin.

Therefore, in one specific embodiment, the nucleic acid probe is at least one selected from a group consisting of:

an oligonucleotide probe, the sequence of which is shown in SEQ ID NO: 13, for detecting *Mycobacterium tuberculosis*;

an oligonucleotide probe, the sequence of which is shown in SEQ ID NO: 14, for detecting *Mycobacterium avium*;

an oligonucleotide probe, the sequence of which is shown in SEQ ID NO: 15, for detecting a *Mycobacterium* intracellular;

an oligonucleotide probe, the sequence of which is shown in SEQ ID NO: 16, for detecting *Mycobacterium fortuitum*;

an oligonucleotide probe, the sequence of which is shown in SEQ ID NO: 17, for detecting *Mycobacterium abscessus*;

an oligonucleotide probe, the sequence of which is shown in SEQ ID NO: 18, for detecting *Mycobacterium kansasii*;

an oligonucleotide probe, the sequence of which is shown in SEQ ID NO: 19, for detecting T533C wild type of the rpoB gene of *Mycobacterium tuberculosis*;

an oligonucleotide probe, the sequence of which is shown in SEQ ID NO: 2, for detecting T533C mutant of the rpoB gene of *Mycobacterium tuberculosis*;

an oligonucleotide probe, the sequence of which is shown in SEQ ID NO: 20, for detecting C531T wild type of the rpoB gene of *Mycobacterium tuberculosis*;

an oligonucleotide probe, the sequence of which is shown in SEQ ID NO: 21, for detecting C531T mutant of the rpoB gene of *Mycobacterium tuberculosis*;

an oligonucleotide probe, the sequence of which is shown in SEQ ID NO: 22, for detecting 526 wild type of the rpoB gene of *Mycobacterium tuberculosis*;

an oligonucleotide probe, the sequence of which is shown in SEQ ID NO: 23, for detecting C526G mutant of the rpoB gene of *Mycobacterium tuberculosis*;

an oligonucleotide probe, the sequence of which is shown in SEQ ID NO: 24, for detecting C526T mutant of the rpoB gene of *Mycobacterium tuberculosis*;

an oligonucleotide probe, the sequence of which is shown in SEQ ID NO: 25, for detecting A526T mutant of the rpoB gene of *Mycobacterium tuberculosis*;

an oligonucleotide probe, the sequence of which is shown in SEQ ID NO: 26, for detecting A526G mutant of the rpoB gene of *Mycobacterium tuberculosis*;

an oligonucleotide probe, the sequence of which is shown in SEQ ID NO: 27, for detecting A516T wild type of the rpoB gene of *Mycobacterium tuberculosis*;

an oligonucleotide probe, the sequence of which is shown in SEQ ID NO: 28, for detecting A516T mutant of the rpoB gene of *Mycobacterium tuberculosis*;

an oligonucleotide probe, the sequence of which is shown in SEQ ID NO: 29, for detecting T511C wild type of the rpoB gene of *Mycobacterium tuberculosis*;

an oligonucleotide probe, the sequence of which is shown in SEQ ID NO: 30, for detecting T511C mutant of the rpoB gene of *Mycobacterium tuberculosis*;

a nucleic acid probe, the nucleotide sequence of which is shown in SEQ ID NO: 35, for detecting HPV genotype 16;

a nucleic acid probe, the nucleotide sequence of which is shown in SEQ ID NO: 36, for detecting HPV genotype 18;

a nucleic acid probe, the nucleotide sequence of which is shown in SEQ ID NO: 37, for detecting HPV genotype 31;

a nucleic acid probe, the nucleotide sequence of which is shown in SEQ ID NO: 38, for detecting HPV genotype 33;

a nucleic acid probe, the nucleotide sequence of which is shown in SEQ ID NO: 39, for detecting HPV genotype 35;

a nucleic acid probe, the nucleotide sequence of which is shown in SEQ ID NO: 40, for detecting HPV genotype 39;

a nucleic acid probe, the nucleotide sequence of which is shown in SEQ ID NO: 41, for detecting HPV genotype 45;

a nucleic acid probe, the nucleotide sequence of which is shown in SEQ ID NO: 42, for detecting HPV genotype 51;

a nucleic acid probe, the nucleotide sequence of which is shown in SEQ ID NO: 43, for detecting HPV genotype 52;

a nucleic acid probe, the nucleotide sequence of which is shown in SEQ ID NO: 44, for detecting HPV genotype 56;

a nucleic acid probe, the nucleotide sequence of which is shown in SEQ ID NO: 45, for detecting HPV genotype 58;

a nucleic acid probe, the nucleotide sequence of which is shown in SEQ ID NO: 46, for detecting HPV genotype 59; and a nucleic acid probe, the nucleotide sequence of which is shown in SEQ ID NO: 47, for detecting HPV genotype 68.

According to one specific embodiment of the present disclosure, the PCR reagent further includes Taq DNA polymerase, 4×dNTPs (dATP, dCTP, dGTP, and dTTP), a buffer solution, magnesium ions, and other essential components. The buffer solution can be 10-50 mmol/L Tris-HCl buffer solution, and the concentration of the magnesium ions can be in the range from 1.5 to 2.5 mM, preferably being 2 mM.

The present disclosure further provides a method of detecting a target nucleic acid in a sample, comprising:

step C1): performing, in a hybridization solution containing alkaline phosphatase labeled-streptavidin, one-step reaction between at least one nucleic acid probe immobilized on a surface of a solid support and a biotin-labeled target nucleic acid, wherein the hybridization solution contains therein a non-ionic surfactant, a cationic polymer, and a buffer solution having a pH value in the range from 6.5 to 8.5; and step E1): contacting the surface of the solid support, after the reaction in step C1), with a color developing buffer solution containing a color developing substrate and having a pH value in the range from 9.0 to 10.0 for a color developing reaction, to detect the target nucleic acid contained in the sample; or step C2): performing, in a hybridization solution containing alkaline phosphatase labeled-streptavidin, one-step reaction between at least one target nucleic acid immobilized on a surface of a solid support and a biotin-labeled nucleic acid probe, wherein the hybridization solution contains therein a non-ionic surfactant, a cationic polymer, and a buffer solution having a pH value in the range from 6.5 to 8.5; and step E2): contacting the surface of the solid support, after the reaction in step C2), with a color developing buffer solution containing a color developing substrate and having a pH value in the range from 9.0 to 10.0 for a color developing reaction, to detect the target nucleic acid contained in the sample.

Furthermore, the above buffer solution having a pH value in the range from 6.5 to 8.5 can be 3×SSC buffer solution having a pH value in the range from 6.5 to 8.5, or a phosphate buffer solution having a pH value in the range from 6.5 to 8.5.

In the present disclosure, the concentration of the alkaline phosphatase labeled-streptavidin in the hybridization solution constitutes an important aspect. The inventors of the present disclosure have discovered, after extensive experiments and creative work, if the concentration of the alkaline phosphatase labeled-streptavidin in the hybridization solution is too low, the detection sensitivity of the target nucleic acid will be affected; while if the concentration of the alkaline phosphatase labeled-streptavidin in the hybridization solution is too high, a nonspecific adsorption phenomenon will easily occur, thus affecting the accuracy of detection results of the target nucleic acid. Thus, in one specific embodiment of the present disclosure, the concentration of the alkaline phosphatase labeled-streptavidin in the hybridization solution is in the range from 0.05 to 2 µg/ml, preferably from 0.1 to 1.5 µg/ml, and more preferably from 0.5 to 1.2 µg/ml. According to the method of the present disclosure, the concentration of the alkaline phosphatase labeled-streptavidin in the hybridization solution can be, but is not limited to 0.05 µg/ml, 0.06 µg/ml, 0.07 µg/ml, 0.08 µg/ml, 0.09 µg/ml, 0.1 µg/ml, 0.2 µg/ml, 0.3 g/ml, 0.4 µg/ml, 0.5 µg/ml, 0.6 µg/ml, 0.7 µg/ml, 0.8 µg/ml, 0.9 µg/ml, 1 µg/ml, 1.1 g/ml, or 1.2 µg/ml.

In one specific embodiment, the concentration of the biotin-labeled nucleic acid probe or the biotin-labeled nucleic acid in the hybridization solution is in the range from 0.1 to 5 pmol/ml, preferably from 0.2 to 2 pmol/ml, and more preferably from 0.25 to 1 pmol/ml. The inventors of the present disclosure have discovered, after extensive experiments and inventive labor, examples of concentrations of the biotin-labeled nucleic acid probe or biotin-labeled nucleic acid in the hybridization solution according to the present disclosure include, but are not limited to 0.1 pmol/ml, 0.2 pmol/ml, 0.3 pmol/ml, 0.4 pmol/ml, 0.5 pmol/ml, 0.6 pmol/ml, 0.7 pmol/ml, 0.8 pmol/ml, 0.9 pmol/ml, 1.0 pmol/ml, 2 pmol/ml, 3 pmol/ml, 4 pmol/ml, and 5 pmol/ml.

In one specific embodiment, the cationic polymer is at least one selected from a group consisting of cationic polyacrylamide, polylysine, and polyaluminum chloride.

In one specific embodiment, in the hybridization solution, the concentration of the non-ionic surfactant is in the range from 0.01% to 2% (v/v), preferably from 0.05% to 1% (v/v), and the concentration of the cationic polymer is in the range from 0.01% to 0.5% (w/v), preferably from 0.05% to 0.2% (w/v).

In one specific embodiment, the hybridization solution further contains therein zinc ions and/or magnesium ions. The concentration of the zinc ions in the hybridization solution is preferably in the range from 0.001 to 0.1 mol/L, more preferably from 0.005 to 0.05 mol/L. The concentration of the magnesium ions in the hybridization solution is preferably in the range from 0.001 to 0.1 mol/L, more preferably from 0.005 to 0.05 mol/L, In one specific embodiment, the hybridization solution further contains therein a protein, which is at least one selected from a group consisting of albumin, casein, and gelatin. The concentration of the protein is preferably in the range from 0.1% to 10% (w/v), more preferably in the range from 1% to 5% (w/v).

In one specific embodiment, the hybridization solution does not contain therein ethylenediamine tetraaetate, inorganic phosphate, or ethanolamine.

In one specific embodiment, the color developing solution further contains therein a $C_8$-$C_{18}$ alkylglucoside, preferably a $C_9$-$C_{13}$ alkylglucoside.

In one specific embodiment, the concentration of the alkylglucoside is in the range from 0.01% to 0.5% (w/v), preferably in the range from 0.05% to 0.1% (w/v).

In one specific embodiment, the pH value of the buffer solution contained in the hybridization solution is the range from 6.8 to 7.2, preferably being 7.0; and/or the pH value of the color developing solution is in the range from 9.3 to 9.7, preferably being 9.5.

In one specific embodiment, in step E1) or E2), the color developing solution flows to contact the surface of the solid support for color development, at a flow rate in the range from 0.2 to 1.2 cm/s, in a period ranging from 2 to 30 min, preferably from 5 to 20 min, and more preferably from 8 to 15 min.

In one specific embodiment, in step C1) or C2), the reaction temperature is in the range from 35 to 50° C., preferably from 37 to 42° C., and the reaction time is in the range from 5 to 30 min, preferably from 10 to 15 min.

In one specific embodiment, the method further comprises, before step C1):

step A1): pretreating the surface of the solid support with a pretreatment solution, wherein the pretreatment solution contains a Tris-HCl buffer solution having a pH value in the range from 7.0 to 8.0, NaCl, a sealant, and a non-ionic surfactant; and step B1): preliminarily treating the surface of the solid support with a preliminary treatment solution, wherein the preliminary treatment solution contains NaCl and a buffer solution having a pH value in the range from 7.0 to 9.0, which is selected from a group consisting of barbital sodium-hydrochloric acid buffer solution, Tris-HCl buffer solution, glycine-sodium hydroxide buffer solution, and borate-borax buffer solution; or the method further comprises, before step C2):

step A2): pretreating the surface of the solid support with a pretreatment solution, wherein the pretreatment solution contains a Tris-HCl buffer solution having a pH value in the range from 7.0 to 8.0, NaCl, a sealant, and a non-ionic surfactant; and step B2): preliminarily treating the surface of the solid support with a preliminary treatment solution, wherein the preliminary treatment solution contains NaCl and a buffer solution having a pH value in the range from 7.0 to 9.0, which is selected from a group consisting of barbital sodium-hydrochloric acid buffer solution, Tris-HCl buffer solution, glycine-sodium hydroxide buffer solution, and borate-borax buffer solution.

In one specific embodiment, the sealant is casein and/or bovine serum albumin, and the non-ionic surfactant is TWEEN (Polysorbate) and/or TRITON (Octoxynol). The concentration of the sealant in the pretreatment solution is in the range from 1% to 5% (w/v), preferably from 2% to 4%, and the concentration of the non-ionic surfactant in the pretreatment solution is in the range from 0.05% to 0.1% (v/v), preferably from 0.05% to 0.2% (v/v).

In one specific embodiment, the pretreatment solution further contains therein an anionic dispersant and/or anionic polyacrylamide.

In one specific embodiment, the anionic dispersant is selected from lignosulphonates, preferably being sodium lignosulphonate. The concentration of the anionic dispersant is preferably in the range from 0.05% to 0.2% (w/v), more preferably from 0.1% to 0.15% (w/v).

In one specific embodiment, the concentration of anionic polyacrylamide is in the range from 0.02% to 0.5% (w/v), preferably from 0.1% to 0.3% (w/v).

In one specific embodiment, the method further comprises:

step D1): performing, after step C1) and before step E1), aftertreatment on the surface of the solid support with an aftertreatment solution, which contains a buffer solution having a pH value in the range from 9.0 to 10.0; or alternatively step D2): performing, after step C2) and before step E2), aftertreatment on the surface of the solid support with an aftertreatment solution, which contains a buffer solution having a pH value in the range from 9.0 to 10.0.

In one specific embodiment, the aftertreatment solution further contains therein magnesium ions, e.g., magnesium chloride and/or magnesium sulfate, and/or a $C_8$-$C_{18}$alkylglucoside, preferably magnesium ions and/or a $C_9$-$C_{13}$ alkylglucoside.

In one specific embodiment, the alkylglucoside has a concentration in the range from 0.1% to 5% (w/v), preferably from 0.5% to 2% (w/v).

In one specific embodiment, the nucleic acid probe used in step C1) or step C2) is selected from oligonucleotide probes each having 15 to 40 bases, preferably oligonucleotide probes each having 16 to 25 bases.

In one specific embodiment, the nucleic acid probe is at least one selected from a group consisting of:

an oligonucleotide probe, the sequence of which is shown in SEQ ID NO: 13, for detecting *Mycobacterium tuberculosis;* an oligonucleotide probe, the sequence of which is shown in SEQ ID NO: 14, for detecting *Mycobacterium avium;* an oligonucleotide probe, the sequence of which is shown in SEQ ID NO: 15, for detecting a *Mycobacterium* intracellular;

an oligonucleotide probe, the sequence of which is shown in SEQ ID NO: 16, for detecting *Mycobacterium fortuitum;* an oligonucleotide probe, the sequence of which is shown in SEQ ID NO: 17, for detecting *Mycobacterium abscessus;* an oligonucleotide probe, the sequence of which is shown in SEQ ID NO: 18, for detecting *Mycobacterium kansasii;* an oligonucleotide probe, the sequence of which is shown in SEQ ID NO: 19, for detecting T533C wild type of the rpoB gene of *Mycobacterium tuberculosis;* an oligonucleotide probe, the sequence of which is shown in SEQ ID NO: 2, for detecting T533C mutant of the rpoB gene of *Mycobacterium tuberculosis;* an oligonucleotide probe, the sequence of which is shown in SEQ ID NO: 20, for detecting C531T wild type of the rpoB gene of *Mycobacterium tuberculosis;* an oligonucleotide probe, the sequence of which is shown in SEQ ID NO: 21, for detecting C531T mutant of the rpoB gene of *Mycobacterium tuberculosis;* an oligonucleotide probe, the sequence of which is shown in SEQ ID NO: 22, for detecting 526 wild type of the rpoB gene of *Mycobacterium tuberculosis;* an oligonucleotide probe, the sequence of which is shown in SEQ ID NO: 23, for detecting C526G mutant of the rpoB gene of *Mycobacterium tuberculosis;* an oligonucleotide probe, the sequence of which is shown in SEQ ID NO: 24, for detecting C526T mutant of the rpoB gene of *Mycobacterium tuberculosis;* an oligonucleotide probe, the sequence of which is shown in SEQ ID NO: 25, for detecting A526T mutant of the rpoB gene of *Mycobacterium tuberculosis;* an oligonucleotide probe, the sequence of which is shown in SEQ ID NO: 26, for detecting A526G mutant of the rpoB gene of *Mycobacterium tuberculosis;* an oligonucleotide probe, the sequence of which is shown in SEQ ID NO: 27, for detecting A516T wild type of the rpoB gene of *Mycobacterium tuberculosis;* an oligonucleotide probe, the sequence of which is shown in SEQ ID NO: 28, for detecting A516T mutant of the rpoB gene of *Mycobacterium tuberculosis;* an oligonucleotide probe, the sequence of which is shown in SEQ ID NO: 29, for detecting T511C wild type of the rpoB gene of *Mycobacterium tuberculosis;* an oligonucleotide probe, the sequence of which is shown in SEQ ID NO: 30, for detecting T511C mutant of the rpoB gene of *Mycobacterium tuberculosis*;

a nucleic acid probe, the nucleotide sequence of which is shown in SEQ ID NO: 35, for detecting HPV genotype 16;

a nucleic acid probe, the nucleotide sequence of which is shown in SEQ ID NO: 36, for detecting HPV genotype 18;

a nucleic acid probe, the nucleotide sequence of which is shown in SEQ ID NO: 37, for detecting HPV genotype 31;

a nucleic acid probe, the nucleotide sequence of which is shown in SEQ ID NO: 38, for detecting HPV genotype 33;

a nucleic acid probe, the nucleotide sequence of which is shown in SEQ ID NO: 39, for detecting HPV genotype 35;

a nucleic acid probe, the nucleotide sequence of which is shown in SEQ ID NO: 40, for detecting HPV genotype 39;

a nucleic acid probe, the nucleotide sequence of which is shown in SEQ ID NO: 41, for detecting HPV genotype 45;

a nucleic acid probe, the nucleotide sequence of which is shown in SEQ ID NO: 42, for detecting HPV genotype 51;

a nucleic acid probe, the nucleotide sequence of which is shown in SEQ ID NO: 43, for detecting HPV genotype 52;

a nucleic acid probe, the nucleotide sequence of which is shown in SEQ ID NO: 44, for detecting HPV genotype 56;

a nucleic acid probe, the nucleotide sequence of which is shown in SEQ ID NO: 45, for detecting HPV genotype 58;

a nucleic acid probe, the nucleotide sequence of which is shown in SEQ ID NO: 46, for detecting HPV genotype 59; and a nucleic acid probe, the nucleotide sequence of which is shown in SEQ ID NO: 47, for detecting HPV genotype 68.

In the test kit of the present disclosure, the alkaline phosphatase is a homodimeric protein, which is a zinc-containing metalloenzyme and contains at least two zinc atoms in each molecule. The alkaline phosphatase contains thereon three types of metal-binding sites, i.e., catalytic binding sites, structural binding sites, and regulatory binding sites. The binding of two catalytic binding sites will only result in the phosphorylation of one subunit, i.e., interaction between negative cooperative subunits occurs.

In the test kit of the present disclosure, the biotin has two cyclic structures I and II, of which, structure I is an imidazolone ring, and a main binding part between the biotin and alkaline phosphatase labeled-streptavidin, while structure II is a thiophene ring and has a valeric acid side chain bound to C2 thereof. The biotin molecule is, through a carboxyl group at its terminal, bound to the target nucleic acid of the present disclosure, so as to label the target nucleic acid.

In the test kit of the present disclosure, the streptavidin is a protein secreted by *Streptomyces*. A streptavidin molecule comprises four identical peptide chains, each capable of being bound to one biotin, such that each streptavidin molecule can be bound to four biotin molecules. In addition, in the amino acid composition of each peptide chain, glycine and alanine have relatively large contents, and tryptophan residues in the peptide chain constitute active groups connecting the biotin. The affinity binding constant (K) between the streptavidin and the biotin is 1015 L/mol. In the method of the present disclosure, while the target nucleic acid hybridizes with the nucleic acid probe, affinity binding also occurs between the streptavidin and the biotin, such that alkaline phosphatase labeled-streptavidin molecules in the hybridization solution compete with nucleic acid probe molecules immobilized on the surface of the solid support, to be bound to the biotin-labeled target nucleic acid in the one-step reaction.

Those skilled in the art know how to select a suitable procedure to treat the solid support and a suitable procedure to immobilize the nucleic acid probe on the surface of the solid support of the present disclosure.

In the test kit of the present disclosure, the "nucleic acid probe" refers to a nucleic acid fragment immobilized on the surface of the solid support in a nucleic acid containing a base sequence complementary to a target sequence. The nucleic acid probe has a sequence complementary to at least one portion of the sequence of the target nucleic acid, and thus can hybridize with the at least one portion of the sequence of the target nucleic acid under suitable conditions.

In the test kit of the present disclosure, the "target nucleic acid" refers to a nucleic acid having a target sequence, and can be derived from the organisms listed above or tissues of the organisms listed above. Specifically, the target nucleic acid can, for example, be a genomic nucleic acid sample of *Mycobacterium tuberculosis* contained in sputum, blood, bronchial washings, ascites, or cerebrospinal fluid of an object to be detected.

The target nucleic acid can be extracted from a clinical sample, with the test kit of the present disclosure through a conventional nucleic acid extraction procedure, or with a commercially available nucleic acid extraction kit.

According to the test kit of the present disclosure, not only nucleic acid hybridization and ELISA are combined into one step through direct addition of alkaline phosphatase labeled-streptavidin into the hybridization solution, but film washing and color development can also be combined into one step, thus avoiding a large number of washing steps and reaction solutions. As a result, a conventional molecular hybridization technology, especially the reverse molecular hybridization technology becomes a mode easy to operate. The test kit of the present disclosure has the following advantages: 1) convenient operations; 2) substantially reduced experimental errors; 3) significantly saved experimental time and reagents; and 4) largely improved detection throughput of a nucleic acid in a sample, and high specificity of detection results obtained thereby.

BRIEF DESCRIPTION OF THE DRAWINGS

In order to explain the technical solution contained in the embodiments of the present disclosure more explicitly, the accompanying drawings referred to in describing the embodiments will be simply introduced below. Apparently, these accompanying drawings as briefly described below constitute only some embodiments of the present disclosure. Those of ordinary skill in the art can acquire other drawings based on these accompanying drawings without any creative work. In the drawings.

DETAILED DESCRIPTION OF THE EMBODIMENTS

Figure 1:
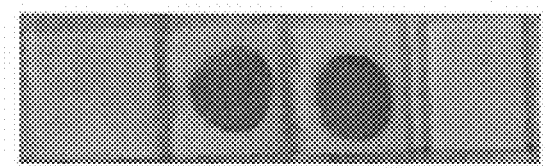
FIG. 1 shows a color development result of Example 7 of the present disclosure.
Figure 2:
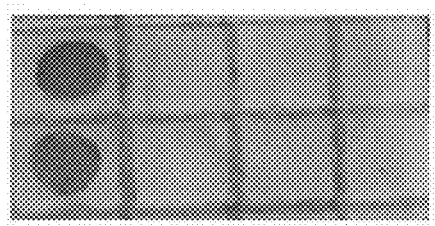
FIG. 2 shows a color development result of Example 13 of the present disclosure.

Particular embodiments of the present disclosure will be described in detail in the following with reference to examples, which, those of skill in the art will understand, are used herein only to describe but not to limit the present disclosure. Where specific conditions are not indicated in the examples, conventional conditions or those proposed by manufactures will be observed. Where the manufactures are not indicated for any reagents or instruments used, these reagents or instruments are conventional products that are commercially available.

In the following examples, the concentrations of bovine serum albumin (hereinafter BSA for short), cationic polyacrylamide (hereinafter CPAM for short), alkaline phosphatase labeled-streptavidin (hereinafter SA-AP for short), sodium lignosulphonate (hereinafter SLS for short), polylysine (hereinafter PLL for short), anionic polyacrylamide (hereinafter APAM for short), sodium lignosulphonate (hereinafter SLS for short), polyethylene glycol 8000, and alkylglucoside refer to corresponding weight volume percentages (w/v) with g/ml as the unit; while the concentrations of TWEEN-20 (Polysorbate-20) and TRITON X-100 (Octoxynol-9) refer to corresponding volume percentages (v/v).

Some reagents used in the present disclosure are listed as follows:

BSA: purchased from Sigma-Aldrich Corporation;
SA-AP: purchased from Gibco (Life Technologies);
zinc chloride: purchased from Sangon Biotech (Shanghai) Co., Ltd.;
magnesium chloride hexahydrate: purchased from Sangon Biotech (Shanghai) Co., Ltd.;
tris base: purchased from Sangon Biotech (Shanghai) Co., Ltd.;
NaCl: purchased from Sangon Biotech (Shanghai) Co., Ltd.;
C8-C18 alkylglucoside: purchased from Sangon Biotech (Shanghai) Co., Ltd;
TWEEN-20 (Polysorbate-20): purchased from Sangon Biotech (Shanghai) Co., Ltd.;
polyethylene glycol 8000: purchased from Sangon Biotech (Shanghai) Co., Ltd.;
PLL: purchased from Sangon Biotech (Shanghai) Co., Ltd.;
CPAM: purchased from Sangon Biotech (Shanghai) Co., Ltd.;
polyaluminum chloride: purchased from Sangon Biotech (Shanghai) Co., Ltd.;
nitrocellulose membrane: purchased from Millipore Corporation, of 0.45 µm pore size, and cut into 2 cm*1 cm pieces for use;
terminal deoxynucleotidyl transferase (TdT enzyme): 5 U/µl, 100 µl, and purchased from Shanghai Jiang & Lai Biological Technology Co., Ltd.;
10×TdT buffer solution: used with TdT enzyme, and supplied by Shanghai Jiang & Lai Biological Technology Co., Ltd.;
dTTP: 100 mmol/L, purchased from Promega Corporation;
Go Taq enzyme: 5 µ/µl, purchased from Promega Corporation;
10×Taq enzyme reaction buffer solution: purchased from Promega Corporation;
MgCl2: 25 mM, purchased from Promega Corporation, and used in PCR;
dNTPs Mix: 10 mM, purchased from Promega Corporation;
nitro blue tetrazolium (NBT): purchased from Sangon Biotech (Shanghai) Co., Ltd.;
5-bromo-4-chloro-3-indolyl-phosphoric acid (BCIP): purchased from Sangon Biotech (Shanghai) Co., Ltd.;
SLS: purchased from Sigma-Aldrich Corporation;
APAM: with molecular weight in the range from 8-15 million, and purchased from Sangon Biotech (Shanghai) Co., Ltd.; and
20×SSC solution: having a pH value of 7.0 and comprising 3.0 mol/L NaCl and 0.3 mol/L sodium citrate.

EXAMPLE 1

Procedure 1 Immobilization of Nucleic Acid Probes on a Surface of a Solid Support 1.1 Experimental Materials The experimental materials used in this procedure included: *Mycobacterium tuberculosis* drug-resistance gene mutation detecting probes, the nucleotide sequences of which were shown in SEQ ID NOs: 1-2, for detecting mutations in the rpoB gene of *Mycobacterium tuberculosis* at codon 533; a positive control probe, the nucleotide sequence of which was shown in SEQ ID NO: 3; and a negative control probe, the nucleotide sequence of which was shown in SEQ ID NO: 4. The above four types of nucleic acid probes were respectively added with water to prepare into 100 µM (i.e., 100 pmol/µl) solutions for use.

In addition, a solid support, i.e., nitrocellulose membrane, was cut into 2 cm*1 cm pieces for use.

1.2 Experimental Steps 1.2.1 Tailing of the Nucleic Acid Probes

For each of the above four types of 100 µM nucleic acid probe solutions, 2 µl, i.e., 200 pmol of a corresponding nucleic acid probe, was collected and added into 100 µl of 100 nmol/L dTTP solution containing 60 U of TdT enzyme and 1×TdT reaction buffer solution, followed by incubation at 37° C. for 60 min. 100 µl of 10 mmol/L EDTA was then added into the resulting solution to terminate the reaction (the final concentration of the probe was 1 pmol/µl).

1.2.2 Immobilization of the Nucleic Acid Probes on the Surface of a Solid Support The above tailed nucleic acid probes (1 pmol/µl), positive control probe and negative control probe solutions were each collected in a volume of 1 µl (each containing 1 pmol of a corresponding probe) and spotted to a nitrocellulose membrane, which was then placed on a piece of paper wetted with TE, followed by immobilization through 10-minute UV light (254 nm wavelength) irradiation.

The arrangement order of the nucleic acid probes on the surface of the nitrocellulose membrane was described in Table 1 as follows.

TABLE 1

| probe for detecting | probe for detecting | Positive control probe | Negative control probe |
|---|---|---|---|
| T533C wild type | T533C mutant | | |

Procedure 2 Amplification of Target Nucleic Acids 2.1 Experimental Materials

The experimental materials used in this procedure included:

target nucleic acids: 0.01 ng/µl *Mycobacterium tuberculosis* (which was, as confirmed through sequencing, subjected to T533C mutation in the rpoB gene thereof) genomic nucleic acid and 50 ng/µl human genomic nucleic acid;

a primer pair for amplification of the rpoB gene of *Mycobacterium tuberculosis*, of which, an upstream primer had a nucleotide sequence as shown in SEQ ID NO: 5, a biotin-labeled 5' end, and a concentration of 0.2 μM, while a downstream primer had a nucleotide sequence as shown in SEQ ID NO: 6, and a concentration of 0.2 μM; and a primer pair for amplification of a human actin gene, of which, an upstream primer had a nucleotide sequence as shown in SEQ ID NO: 7, and a biotin-labeled 5' end, while a downstream primer had a nucleotide sequence as shown in SEQ ID NO: 8.

2.2 Experimental Steps 2.2.1 Preparation of a PCR Reaction System

PCR amplification was performed with the *Mycobacterium tuberculosis* genomic nucleic acid and the human genomic nucleic acid as templates, in a 50 μl PCR amplification system comprising:

GoTaq enzyme: 1U;
Taq enzyme reaction buffer solution: 1× (i.e., one time the concentration was used);
an upstream primer as shown in SEQ ID NO: 5: 0.2 μM;
a downstream primer as shown in SEQ ID NO: 6: 0.2 μM;
an upstream primer as shown in SEQ ID NO: 7: 0.2 μM;
a downstream primer as shown in SEQ ID NO: 8: 0.2 μM;
MgCl2: 2.0 mM;
dNTPs Mix: 0.2 mM;
template 1:1 μl of the *Mycobacterium tuberculosis* genomic nucleic acid;
template 2:1 μl of the human genomic nucleic acid; and
water as a balance.

2.2.2 PCR Amplification Reactions

Pre-denaturation was first performed at 95° C. for 5 min, which preceded performance of 35 cycles of pre-denaturation at 95° C. for 1.5 min, at 55° C. for 1.5 min, and at 72° C. for 1 min, and finally an extension performed at 72° C. for 5 min.

2.2.3 Denaturation of a PCR Product

Incubation was first performed at 95° C. for 10 min, followed by a five-minute ice bath.

Procedure 3 One-step Reaction 3.1 Preparation of a Hybridization Solution

The hybridization solution included the following components: a 3×SSC solution having a pH value of 7.0, 1 μg/ml SA-AP, 0.5% TWEEN-20 (Polysorbate-20), 0.1% PLL, and water as a balance.

3.2 One-step Reaction

The nitrocellulose membrane immobilized with the nucleic acid probes on the surface thereof, as obtained in procedure 1, was placed into 1 ml of the hybridization solution, in which, 10 μl of the denatured PCR product as obtained in procedure 2 was simultaneously added, followed by 15-minute reactions at the temperature of 37° C. after homogeneous mixing.

Procedure 4 Color Development Reaction 4.1 Preparation of a Color Developing Solution The color developing solution included the following components: 0.1 mol/L Tris-HCl having a pH value of 9.5, 50 mM MgCl2, 0.33 mg/ml NBT, 0.17 mg/ml BCIP, 0.07% n-dodecylglucoside, and water as a balance.

4.2 Color Development Reaction

The nitrocellulose membrane was clamped, after the reaction of procedure 3, with tweezers, to allow the surface thereof immobilized with the nucleic acid probes to face upward, and was tilted slightly, such that one end of the membrane was higher than the other. The color developing solution was then drawn with a pipette and continuously dropped from above an upper end of the membrane, so as to continuously flow through the surface of the nitrocellulose membrane from the top down, i.e., the color developing solution entered the membrane from the upper end, and exited from a lower end thereof, at a flow rate in the range from 0.2 to 1.2 cm/s in 10 min. Color development results were then observed.

The color development results of this example were shown in Table 5.

The results indicated that the probe for detecting T533C mutant was strong positive, while the probe for detecting T533C wild type was negative. It could thus be confirmed that a T→C nucleic acid base mutation occurred in the rpoB gene of the *Mycobacterium tuberculosis* genome at codon 533. At the same time, the positive control point showed positive, and the negative control point showed negative, indicating normal test results of the experiment.

EXAMPLE 2

The cationic polymer in the hybridization solution was replaced with CPAM having a final concentration of 0.5%.

Other conditions and procedures were respectively the same as those in Example 1.

The color development results of this example were shown in Table 5.

EXAMPLE 3

The cationic polymer in the hybridization solution was replaced with polyaluminum chloride having a final concentration of 0.2%.

Other conditions and procedures were respectively the same as those in Example 1.

The color development results of this example were shown in Table 5.

EXAMPLE 4

The conditions and procedures were respectively the same as those in Example 1, except that the hybridization solution was added with ZnCl2 having a final concentration final concentration of 10 mM.

The color development results of this example were shown in Table 5.

EXAMPLE 5

The conditions and procedures were respectively the same as those in Example 1, except that the hybridization solution was added with MgCl2 having a final concentration final concentration of 10 mM.

The color development results of this example were shown in Table 5.

EXAMPLE 6

The conditions and procedures were respectively the same as those in Example 1, except that the hybridization solution was added with ZnCl2 and MgCl2, the final concentrations of which were both 10 mM.

The color development results of this example were shown in Table 5.

EXAMPLE 7

The conditions and procedures were respectively the same as those in Example 6, except that the hybridization solution was added with BSA having a final concentration of 2%, and polyethylene glycol 8000 having a final concentration of 2%.

The color development results of this example were shown in FIG. 1 and Table 5.

EXAMPLE 8

The conditions and procedures in this example were respectively the same as those in Example 7, except that the color developing solution did not contain alkylglucoside or MgCl2 therein.

The color development results of this example were shown in Table 5.

EXAMPLE 9

The conditions and procedures in this example were respectively the same as those in Example 7, except that the color developing solution did not contain MgCl2 therein.

The color development results of this example were shown in Table 5.

EXAMPLE 10

The conditions and procedures in this example were respectively the same as those in Example 1, except that the color developing solution did not contain alkylglucoside or MgCl2 therein.

The color development results of this example were shown in Table 5.

EXAMPLE 11

The conditions and procedures in this example were respectively the same as those in Example 6, except that the pH value of the buffer solution used in the hybridization solution was 6.5, and the concentrations of SA-AP, the non-ionic surfactant, the cationic polymer, the zinc ions, and magnesium ions in the hybridization solution were 0.05 μg/ml, 0.01% (v/v), 0.01% (w/v), 0.001 mol/L, and 0.001 mol/L, respectively.

The color development results of this example were shown in Table 6.

EXAMPLE 12

The conditions and procedures in this example were respectively the same as those in Example 6, except that the pH value of the buffer solution used in the hybridization solution was 8.5, and the concentrations of SA-AP, the non-ionic surfactant, the cationic polymer, the zinc ions, and the magnesium ions in the hybridization solution were 2 μg/ml, 2% (v/v), 0.5% (w/v), 0.1 mol/L, and 0.1 mol/L, respectively.

The color development results of this example were shown in Table 6.

EXAMPLE 13

The conditions and procedures in this example were respectively the same as those in Example 6, except that, in the hybridization solution, the final concentrations of SA-AP, the non-ionic surfactant, the cationic polymer, the zinc ions, and the magnesium ions were 1.2 μg/ml, 1% (v/v), 0.2% (w/v), 0.05 mol/L, and 0.05 mol/L, respectively.

The color development results of this example were shown in Table 6.

EXAMPLE 14

The conditions and procedures in this example were respectively the same as those in Example 13, except that, in the hybridization solution, the final concentration of n-hexadecylglucoside was 0.01 μg/ml.

The color development results of this example were shown in Table 6.

EXAMPLE 15

The conditions and procedures in this example were respectively the same as those in Example 13, except that, in the hybridization solution, the final concentration of n-octylalkylglucoside was 0.5 μg/ml.

The color development results of this example were shown in Table 6.

EXAMPLE 16

The conditions and procedures in this example were respectively the same as those in Example 13, except that, in the hybridization solution, the final concentration of n-dodecylglucoside was 0.05 μg/ml.

The color development results of this example were shown in Table 6.

EXAMPLE 17

The conditions and procedures in this example were respectively the same as those in Example 13, except that, in the hybridization solution, the final concentration of n-dodecylglucoside was 0.1 μg/ml.

The color development results of this example were shown in Table 6.

EXAMPLE 18

Procedure 1 Immobilization of Target DNA on the Surface of a Solid Support 1.1 Experimental Materials The experimental materials used in this procedure included:

a solid support: nitrocellulose membrane, which was cut into four 2 cm*1 cm pieces for use, labeled A1, B1, C1, and D1, respectively;

target DNA-containing samples to be tested: whole genome plasmid standards of HPV type 16 (1 pg/μl and 0.1 pg/μl), type 18 (1 pg/μl and 0.1 pg/μl), type 6 (1 pg/μl and 0.1 pg/μl), and type 11 (1 pg/μl and 0.1 pg/μl), which were supplied by Shanghai General Biotech Co., Ltd.; and a denaturing solution: 0.4 mol/L NaOH solution.

In addition, a 20×SSC buffer solution was diluted into a 15×SSC buffer solution and a 10×SSC buffer solution, respectively, for use.

1.2 Experimental Steps 2.2.1 Pretreatment of the Nitrocellulose Membranes

The nitrocellulose membranes were placed into the 15×SSC buffer solution with tweezers, soaked therein for 15 min, removed therefrom, placed onto filter paper, and dried at 60° C. for 1.5 h.

1.2.2 Immobilization of the Target DNA on the Surfaces of the Nitrocellulose Membranes Whole genome plasmid solutions of HPV types 16, 18, 6, and 11 at concentrations of respectively 10 pg/μl and 1 pg/μl were each collected in a volume of 1 μl, spotted to each of the nitrocellulose membranes, and dried at room temperature.

The layout of the samples to be tested on the surface of each of the above four nitrocellulose membranes labeled A1, B1, C1, and D1 was shown in Table 2 below.

TABLE 2

| HPV type 16: 1 pg/μl | HPV type 18: 1 pg/μl | HPV type 6: 1 pg/μl | HPV type 11: 1 pg/μl |
|---|---|---|---|
| HPV type 16: 0.1 pg/μl | HPV type 18: 0.1 pg/μl | HPV type 6: 0.1 pg/μl | HPV type 11: 0.1 pg/μl |

1.2.3 Denaturation

The nitrocellulose membranes were soaked in the denaturing solution for 10 min, the purpose of which was to alter the double strand of the genome into single strands, and thus to facilitate hybridization with DNA probes in subsequent steps.

1.2.4 Neutralization

The denatured nitrocellulose membranes were soaked again into the 10×SSC buffer solution for 10 min.

1.2.5 Drying

The nitrocellulose membranes were taken out of the buffer solution, and excess water was absorbed therefrom with filter paper, followed by one-hour drying at 80° C.

Procedure 2 Pretreatment

2.1 Preparation of a Pretreatment Solution

The pretreatment solution included the components of 0.1 mol/L Tris base having a pH value of 7.5, 1 mol/L NaCl, 2% BSA, 0.1% TWEEN-20 (Polysorbate-20), 0.15% SLS, 0.2% APAM, and water as a balance. The base solutions of the pretreatment solution were 0.1 mol/L Tris-HCl buffer solution having a pH value in the range from 7.0 to 8.0, 1 mol/L NaCl, 2% BSA, and 0.1% TWEEN-20 (Polysorbate-20).

2.2 Pretreatment

The nitrocellulose membranes immobilized with the whole genome plasmid standards of HPV on the surfaces thereof, as obtained in procedure 1, were soaked in the pretreatment solution at 37° C. for 30 min, during which, the nitrocellulose membranes were flipped once.

Procedure 3 Preliminary Treatment

3.1 Preparation of a Preliminary Treatment Solution

The preliminary solution included the components of 0.1 mol/L Tris base having a pH value of 7.5, 1 mol/L NaCl, and water as a balance. The base solutions of the preliminary treatment solution were 0.1 mol/L Tris-HCl buffer solution having a pH value in the range from 7.0 to 9.0, and 1 mol/L NaCl.

3.2 Preliminary Treatment

The four nitrocellulose membranes after the pretreatment in procedure 2 were washed on the surfaces thereof with the preliminary treatment solution three times, each time for 5 min.

Procedure 4 One-step Reaction

4.1 Experimental Materials

The experimental materials used in this procedure included DNA probes, i.e., oligonucleotide probes, the nucleotide sequences of which were shown in SEQ ID NOs: 9-12, for detection of four different HPV gene subtypes. The oligonucleotide probes had biotin-labeled 5' ends, and were synthesized by Sangon Biotech (Shanghai) Co., Ltd. These probes were respectively prepared into 50 pmol/ml aqueous solutions for use.

4.2 Experimental Steps

4.2.1 Preparation of Four DNA Probe-Containing Hybridization Solutions

The nucleotide sequences of the DNA probes were respectively shown in SEQ ID NOs: 9, 10, 11, and 12, and the hybridization solutions were respectively labeled HPV 16-probe, HPV 18-probe, HPV 6-probe, and HPV 11-probe. The four hybridization solutions were each composed of 0.5 pmol/ml HPV DNA probe having a pH value of 7.0, 3×SSC, 20 ng/ml SA-AP, 10 mM ZnCl2, 10 mM MgCl2, 0.3% TWEEN-20 (Polysorbate-20), 0.04% PLL, 5% polyethylene glycol 8000, and water as a balance.

4.2.2 One-step Reaction

The four nitrocellulose membranes, immobilized with whole genome samples of HPV on the surfaces thereof, as treated in the preliminary treatment in procedure 3, were respectively placed in the hybridization solutions, followed by 8-minute reactions at 42° C. in water baths, wherein nitrocellulose membranes A1, B1, C1, and D1 were respectively placed in HPV 16-probe, HPV 18-probe, HPV 6-probe, and HPV 11-probe.

Procedure 5 Aftertreatment

5.1 Preparation of an Aftertreatment Solution

The aftertreatment solution included the components of 0.1 mol/L NaCl, 0.1 mol/L Tris base having a pH value of 9.5, 50 mM MgCl2, and 1% n-dodecylglucoside. The base solutions of the aftertreatment solution were a buffer solution having a pH value of 9.5 and 0.1 mol/L NaCl.

5.2 Aftertreatment

The four nitrocellulose membranes, as obtained after the one-step reaction of procedure 4, were respectively washed with the above aftertreatment solution three times, each time for 5 min.

Procedure 6 Color Development Reaction

6.1 Preparation of a Substrate Solution

The substrate solution included the components of 0.1 mol/L Tris base having a pH value of 9.5, 0.1 mol/L NaCl, 50 mM MgCl2, 0.33 mg/ml NBT, 0.17 mg/ml BCIP, and water as a balance.

6.2 Color Development Reaction

The four nitrocellulose membranes after being treated in the aftertreatment were respectively soaked in the substrate solution for 5-10 minutes of color development. Color development results were then observed.

Figure 3:
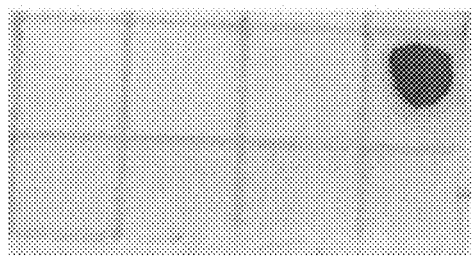
FIG. 3 shows a color development result of Example 18 of the present disclosure.

The color development results of this example were shown in FIG. 3 and Table 7. As indicated in FIG. 3, nitrocellulose membrane A1 could detect out not only a rather clear positive signal of the target DNA of HPV type 16, but also a positive signal of the target DNA of HPV type 16 at a concentration of 0.1 pg/μl. In addition, the detection background of the nitrocellulose membranes was extremely low. Except for the region where the target DNA of HPV type 16 was spotted, none of the regions spotted with the target DNA of other HPV types was colored. As can be seen, the specificity of the method of the present disclosure was relatively high.

The detection effects of nitrocellulose membranes B1, C1, and D1 were similar as the detection effect of nitrocellulose membrane A1.

EXAMPLE 19

The conditions and procedures of this example were respectively the same as those in Example 18, except that the pH value of the buffer solution used in the pretreatment solution and that of the buffer solution used in the preliminary treatment solution were both 7.0.

The color development results of this example were shown in Table 7.

EXAMPLE 20

The conditions and procedures of this example were respectively the same as those in Example 18, except that the pH value of the buffer solution used in the pretreatment solution and that of the buffer solution used in the preliminary treatment solution were respectively 8.0 and 9.0.

The color development results of this example were shown in Table 7.

EXAMPLE 21

The conditions and procedures of this example were respectively the same as those of Example 18, except that procedure 5, i.e., aftertreatment, of Example 18 was cancelled.

The color development results of this example were shown in Table 7.

EXAMPLE 22

The conditions and procedures of this example were respectively the same as those of Example 21, except that the pretreatment solution did not contain SLS or APAM therein.

The color development results of this example were shown in Table 7.

EXAMPLE 23

The conditions and procedures of this example were respectively the same as those of Example 21, except that the pretreatment solution contained SLS at a final concentration of 0.05% and did not contain APAM therein.

The color development results of this example were shown in Table 7.

EXAMPLE 24

The conditions and procedures of this example were respectively the same as those of Example 21, except that the pretreatment solution contained SLS at a final concentration of 2% and did not contain APAM therein.

The color development results of this example were shown in Table 7.

EXAMPLE 25

The conditions and procedures of this example were respectively the same as those of Example 21, except that the pretreatment solution contained SLS at a final concentration of 0.1% and did not contain APAM therein.

The color development results of this example were shown in Table 7.

EXAMPLE 26

The conditions and procedures of this example were respectively the same as those of Example 21, except that the pretreatment solution did not contain SLS and contained APAM at a final concentration of 0.05% therein.

The color development results of this example were shown in Table 7.

EXAMPLE 27

The conditions and procedures of this example were respectively the same as those of Example 21, except that the pretreatment solution did not contain SLS and contained APAM at a final concentration of 0.1%.

The color development results of this example were shown in Table 7.

EXAMPLE 28

The conditions and procedures of this example were respectively the same as those of Example 21, except that the pretreatment solution did not contain SLS and contained APAM at a final concentration of 0.15%.

The color development results of this example were shown in Table 7.

EXAMPLE 29

The conditions and procedures of this example were respectively the same as those of Example 18, except that procedure 2, i.e., pretreatment, and procedure 3, i.e., preliminary treatment of Example 18 were cancelled.

The color development results of this example were shown in Table 7.

EXAMPLE 30

The conditions and procedures of this example were respectively the same as those of Example 18, except that the aftertreatment solution did not contain magnesium chloride therein.

The color development results of this example were shown in Table 7.

EXAMPLE 31

The conditions and procedures of this example were respectively the same as those of Example 18, except that the aftertreatment solution did not contain n-dodecylglucoside therein.

The color development results of this example were shown in Table 7.

EXAMPLE 32

The conditions and procedures of this example were respectively the same as those of Example 18, except that the aftertreatment solution did not contain magnesium chloride or n-dodecylglucoside therein.

The color development results of this example were shown in Table 7.

EXAMPLE 33

Detection of a Clinical Sample

The clinical sample used in this example was a sputum sample obtained from a rifampicin-resistant clinical tuberculosis patient (the rpoB gene of which had, as confirmed through PCR sequencing experiments performed on extracted nucleic acid, a T →C nucleic acid base mutation at codon 533).

Procedure 1 Immobilization of Nucleic Acid Probes on the Surface of a Solid Support 1.1 Experimental Materials The experimental materials used in this procedure included the following nucleic acid probes:

an oligonucleotide probe, the sequence of which was shown in SEQ ID NO: 13, for detecting *Mycobacterium tuberculosis*;

an oligonucleotide probe, the sequence of which was shown in SEQ ID NO: 14, for detecting *Mycobacterium avium*;

an oligonucleotide probe, the sequence of which was shown in SEQ ID NO: 15, for detecting a *Mycobacterium intracellular*;

an oligonucleotide probe, the sequence of which was shown in SEQ ID NO: 16, for detecting *Mycobacterium fortuitum*;

an oligonucleotide probe, the sequence of which was shown in SEQ ID NO: 17, for detecting *Mycobacterium abscessus*;

an oligonucleotide probe, the sequence of which was shown in SEQ ID NO: 18, for detecting *Mycobacterium kansasii*;

an oligonucleotide probe, the sequence of which is shown in SEQ ID NO: 19, for detecting T533C wild type of the rpoB gene of *Mycobacterium tuberculosis*;

an oligonucleotide probe, the sequence of which is shown in SEQ ID NO: 2, for detecting T533C mutant of the rpoB gene of *Mycobacterium tuberculosis*;

an oligonucleotide probe, the sequence of which is shown in SEQ ID NO: 20, for detecting C531T wild type of the rpoB gene of *Mycobacterium tuberculosis*;

an oligonucleotide probe, the sequence of which is shown in SEQ ID NO: 21, for detecting C531T mutant of the rpoB gene of *Mycobacterium tuberculosis*;

an oligonucleotide probe, the sequence of which is shown in SEQ ID NO: 22, for detecting 526 wild type of the rpoB gene of *Mycobacterium tuberculosis*;

an oligonucleotide probe, the sequence of which is shown in SEQ ID NO: 23, for detecting C526G mutant of the rpoB gene of *Mycobacterium tuberculosis*;

an oligonucleotide probe, the sequence of which is shown in SEQ ID NO: 24, for detecting C526T mutant of the rpoB gene of *Mycobacterium tuberculosis*;

an oligonucleotide probe, the sequence of which is shown in SEQ ID NO: 25, for detecting A526T mutant of the rpoB gene of *Mycobacterium tuberculosis*;

an oligonucleotide probe, the sequence of which is shown in SEQ ID NO: 26, for detecting A526G mutant of the rpoB gene of *Mycobacterium tuberculosis*;

an oligonucleotide probe, the sequence of which is shown in SEQ ID NO: 27, for detecting A516T wild type of the rpoB gene of *Mycobacterium tuberculosis*;

an oligonucleotide probe, the sequence of which is shown in SEQ ID NO: 28, for detecting A516T mutant of the rpoB gene of *Mycobacterium tuberculosis*;

an oligonucleotide probe, the sequence of which is shown in SEQ ID NO: 29, for detecting T511C wild type of the rpoB gene of *Mycobacterium tuberculosis*;

an oligonucleotide probe, the sequence of which is shown in SEQ ID NO: 30, for detecting T511C mutant of the rpoB gene of *Mycobacterium tuberculosis*;

The experimental materials used in this procedure also included:

a positive control probe, the sequence of which was shown in SEQ ID NOs: 3; and a negative control probe, the sequence of which was shown in SEQ ID NOs: 4.

The dry powder of each of the above 21 probes, including the 6 probes for detecting mycobacteria, the 13 probes for detecting mutations of the rpoB gene, the positive control probe, and the negative control probe, was prepared, with sterilized pure water, into a 100 μM probe solution.

In addition, a solid support, i.e., nitrocellulose membrane, was cut into 2 cm*1 cm pieces for use.

1.2 Experimental Steps 1.2.1 Tailing of the Nucleic Acid Probes

For each of the above 100 μM nucleic acid probe solutions, 2 μl, i.e., 200 pmol of a corresponding nucleic acid probe, was collected and added into 100 μl of 100 nmol/L dTTP solution containing 60 U of TdT enzyme and 1×TdT reaction buffer solution, followed by incubation at 37° C. for 60 min. 100 μl of 10 mmol/L EDTA was then added into the resulting solution to terminate the reaction (the final concentration of the probe was 1 pmol/μl).

1.2.2 Immobilization of the Nucleic Acid Probes on the Surface of the Solid Support The above tailed nucleic acid probes (1 pmol/μl), positive control probe and negative control probe solutions were each collected in a volume of 1 μl (each containing 1 pmol of a corresponding probe) and spotted to a nitrocellulose membrane, which was then placed on a piece of paper wetted with TE, followed by immobilization through 10-minute UV light (254 nm wavelength) irradiation.

The arrangement order of the nucleic acid probes on the surface of the nitrocellulose membrane was described in Table 3 as follows.

TABLE 3

| Oligonucleotide probe for detecting Mycobacterium tuberculosis (SEQ ID NO: 13) | Oligonucleotide probe for detecting Mycobacterium avium complex (SEQ ID NO: 14) | Oligonucleotide probe for detecting a Mycobacterium intracellular probe (SEQ ID NO: 15) | Oligonucleotide probe for detecting Mycobacterium fortuitum (SEQ ID NO: 16) | Oligonucletideo probe for detecting Mycobacterium abscessus (SEQ ID NO: 17) | Oligonucleotide probe for detecting Mycobacterium kansasii (SEQ ID NO: 18) | Positive control probe (SEQ ID NO: 3) |
|---|---|---|---|---|---|---|
| oligonucleotide probe for detecting T533C wild type (SEQ ID NO: 19) | oligonucleotide probe for detecting T533C mutant (SEQ ID NO: 2) | oligonucleotide probe for detecting C531T wild type (SEQ ID NO: 20) | oligonucleotide probe for detecting C531T mutant (SEQ ID NO: 21) | oligonucleotide probe for detecting 526 wild type (SEQ ID NO: 22) | oligonucleotide probe for detecting C526G mutant (SEQ ID NO: 23) | oligonucleotide probe for detecting C526T mutant (SEQ ID NO: 24) |
| oligonucleotide probe | oligonucleotide probe | oligonucleotide probe | oligonucleotide probe | oligonucleotide probe | oligonucleotide probe | Negative control |

TABLE 3-continued

| for detecting A526T mutant (SEQ ID NO: 25) | for detecting A526G mutant (SEQ ID NO: 26) | for detecting A516T wild type (SEQ ID NO: 27) | for detecting A516T mutant (SEQ ID NO: 28) | for detecting T511C wild type (SEQ ID NO: 29) | for detecting T511C mutant (SEQ ID NO: 30) | probe (SEQ ID NO: 4) |
|---|---|---|---|---|---|---|

Procedure 2 Extraction of Target Nucleic Acids 1 ml of the sputum sample and 1 ml of 4 M NaOH solution were collected to be homogeneously mixed, and then placed at room temperature for 30 min to liquefy the sputum. After being homogeneously mixed, 1 ml of a resulting solution was added into a centrifuge tube for two-minute centrifugation at a rotating speed of 12,000 rpm. The resulting supernatant was abandoned, and 1 ml of saline was added to the resulting precipitate to form a suspension, on which centrifugation was performed for 2 min at a rotating speed of 12,000 rpm. The resulting supernatant was abandoned. For the following steps, reference can be made to the method as disclosed in EP 1407051B1: adding 200 µl of a Tris-EDTA buffer solution (i.e., TE buffer solution having a pH value of 8.0) into the centrifuge tube, followed by oscillation to form a suspension; then adding two glass beads of different specifications, i.e., respectively having a diameter of 200 µm and a diameter of 900 µm, at a weight ratio of 4:1, into the centrifuge tube; performing vortex oscillation for 5 minutes, and placing the centrifuge tube after oscillation into a 90° C. water bath for 10-minute heating, followed by centrifugation at a rotating speed of 12,000 rpm. The resulting supernatant was collected for use.

Procedure 3 Amplification of the Target Nucleic Acid 3.1 Experimental Materials

The experimental materials used in this procedure included:

the target nucleic acid: a nucleic acid extract of the sputum sample from the clinical tuberculosis patient, as extracted in procedure 2; and primer solutions: sterile pure water was used to respectively dissolve the dry powder of a 5' end biotin-labeled upstream primer as shown in SEQ ID NO: 31 and the dry powder of a downstream primer as shown in SEQ ID NO: 32 that were used to amplify 16S rDNA, the dry power of a 5' end biotin-labeled upstream primer as shown in SEQ ID NO: 33 and the dry powder of a downstream primer as shown in SEQ ID NO: 34 that were used to amplify the rpoB gene, and the dry powder of a 5' end biotin-labeled upstream primer as shown in SEQ ID NO: 7 and the dry powder of a downstream primer as shown in SEQ ID NO: 8 that were used to amplify the actin gene, to prepare primer six 100 µM primer solutions.

3.2 Experimental Steps 3.2.1 Preparation of a PCR Reaction System

PCR amplification was performed with the *Mycobacterium tuberculosis* genomic nucleic acid and the human genomic nucleic acid as templates, in a 50 µl PCR amplification system comprising:

Go Taq enzyme: 1U;
Taq enzyme reaction buffer solution: 1×;
primer SEQ ID NO: 31: 0.2 µM;
primer SEQ ID NO: 32: 0.2 µM;
primer SEQ ID NO: 33: 0.2 µM;
primer SEQ ID NO: 34: 0.2 µM;
primer SEQ ID NO: 7: 0.2 µM;
primer SEQ ID NO: 8: 0.2 µM;
MgCl2: 2.0 mM;
dNTPs Mix: 0.2 mM;
template: 1 µl;
template 2:1 µl of the human genomic nucleic acid; and water as a balance.

3.2.2 PCR Amplification Reactions

Pre-denaturation was first performed at 95° C. for 5 min, which preceded performance of 35 cycles of pre-denaturation at 95° C. for 1.5 min, at 55° C. for 1.5 min, and at 72° C. for 1 min, and finally an extension performed at 72° C. for 5 min.

3.2.3 Denaturation of a PCR Product

Incubation was first performed at 95° C. for 10 min, followed by a five-minute ice bath.

Procedure 4 One-step Reaction 4.1 Preparation of a Hybridization Solution

The hybridization solution included the following components: a 3×SSC solution having a pH value of 7.0, 1 µg/ml SA-AP, 10 mM ZnCl2, 10 mM MgCl2, 2% BSA, 0.5% TWEEN-20 (Polysorbate-20), 0.1% PLL, 2% polyethylene glycol 8000, and water as a balance.

4.2 One-step Reaction

The nitrocellulose membrane immobilized with the nucleic acid probes on the surface thereof, as obtained in procedure 1, was placed into 1 ml of the hybridization solution, in which, 10 µl of the denatured PCR product as obtained in procedure 3 was simultaneously added, followed by 15-minute reactions at the temperature of 37° C. after homogeneous mixing.

Procedure 5 Color Development Reaction 5.1 Preparation of a Color Developing Solution The color developing solution included the following components: 0.1 mol/L Tris-HCl having a pH value of 9.5, 50 mM MgCl2, 0.33 mg/ml NBT, 0.17 mg/ml BCIP, 0.07% n-dodecylglucoside, and water as a balance.

5.2 Color Development Reaction

Figure 4:
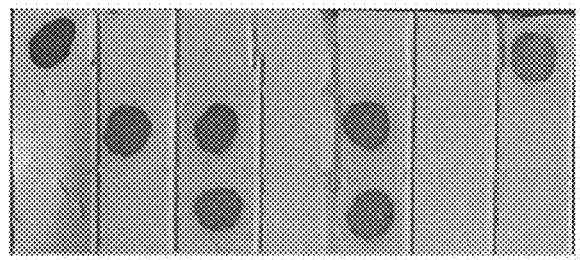
FIG. 4 shows a color development result of Example 33 of the present disclosure.
Figure 5:
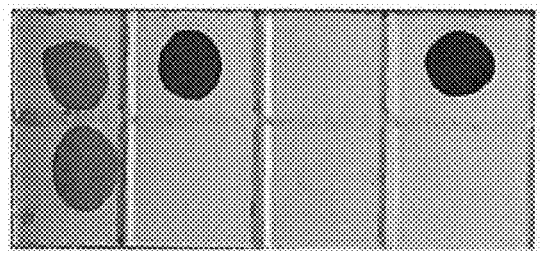
FIG. 5 shows a color development result of Example 34 of the present disclosure.

The nitrocellulose membrane was clamped, after the reaction of procedure 4, with tweezers, to allow the surface thereof immobilized with the nucleic acid probes to face upward, and was tilted slightly, such that a left end of the membrane was higher than a right end thereof. The color developing solution was then drawn with a pipette and continuously dropped from above an upper end of the membrane, so as to continuously flow through the surface of the nitrocellulose membrane from the top down, i.e., the color developing solution entered the membrane from the upper end, and exited from a lower end thereof, in 10 min. Color development results were then observed. The color development results were shown in FIG. 4 and Table 7.

The results indicated that the probe for detecting T533C mutant was strong positive, while the probe for detecting wild type at a corresponding codon was negative. It could thus be confirmed that a T→C nucleic acid base mutation occurred in the rpoB gene of the *Mycobacterium tuberculosis* genome at codon 533. At the same time, the positive control point showed positive, and the negative control point showed negative, indicating normal test results of the experiment. As the tuberculosis patent carried both *Mycobacterium tuberculosis* and human genomic nucleic acids, one sample could be detected to show positive results of both the rpoB gene and the human actin gene.

Example 33 showed that the hybridization detection according to the method of the present disclosure could be performed rapidly and simply, including only two major reaction steps: (1) one-step reaction: while hybridization reaction occurred between one single nucleic acid strand of the biotin-labeled PCR product and the nitrocellulose membrane immobilized with the nucleic acid probe, a streptavidin-biotin binding reaction simultaneously occurred between SA-AP and the biotin-labeled single strand of the PCR product, such that it was possible to form, through a mere one-step reaction, a conjugate of an alkaline phosphatase-labeled nucleic acid hybrid on the surface of the nitrocellulose membrane; and (2) color reaction: the color developing solution was directly dropwise added on the nitrocellulose membrane after the one-step reaction, to generate a color precipitate, while washing off unreacted PCR product, SA-AP, and biotin. The results were then observed. Therefore, the present disclosure has the characteristics of short time consumption, easy operation, high throughput, and low costs, and will largely promote use of the technology of solid-phase molecular hybridization in clinical detection.

EXAMPLE 34

The conditions and procedures of this example were respectively the same as those of Example 31, except that, the PCR reagent also included an enhanced primer pair for enhancing the PCR amplification efficiency of the primer pair, wherein an upstream primer of the enhanced primer pair had a sequence as shown in SEQ ID NO: 48 and a biotin-labeled 5' end, and a downstream primer of the enhanced primer pair had a sequence as shown in SEQ ID NO: 49.

The color development results of this example were shown in Table 7.

EXAMPLE 35

Detection of the Target DNA of Human Papillomavirus in Clinical Samples

The clinical samples used in this example, six altogether, were obtained from cervical exfoliated cell preservation solutions of patients whose clinical cytology examination results were ASCUS or higher scale. These six samples were respectively labeled L1, L2, L3, L4, L5, and L6.

Procedure 1 Extraction of the Target DNA

"Blood tissue cell genome extraction kits," supplied by Tiangen Biotech (Beijing) Co. Ltd., were used to extract nucleic acids that possibly contain the target DNA from the above six clinical cervical exfoliated cell preservation solution samples.

Procedure 2 Immobilization of the Target DNA on the Surface of a Solid Support 2.1 Experimental Materials The experimental materials used in this procedure included:

a solid support: nitrocellulose membrane, which was cut into 2 cm*1 cm pieces for use;

samples to be tested: the six nucleic acid extracts that possibly contain the target DNA, as obtained in procedure 1;

a positive control: a whole genome plasmid standard of human papillomavirus (HPV) type 16 (1 pg/μl), supplied by Shanghai General Biotech Co., Ltd.;

a negative control: salmon sperm DNA, purchased from Beijing JKHD Biotech Co. Ltd. and prepared into a 1 pg/μl solution;

a denaturing solution: 0.4 mol/L NaOH solution; and a 20×SSC buffer solution: having a pH value of 7.0, and including the components of 3.0 mol/L NaCl and a 0.3 mol/L sodium citrate.

In addition, the 20×SSC buffer solution was diluted into a 15×SSC buffer solution and a 10×SSC buffer solution, respectively, for use.

2.2 Experimental Steps 2.2.1 Pretreatment of the Nitrocellulose Membranes

The nitrocellulose membranes were placed into the 15×SSC buffer solution with tweezers, soaked therein for 15 min, removed therefrom, placed onto filter paper, and dried at 60° C. for 1.5 h.

2.2.2 Immobilization of the Target DNA on the Surfaces of the Nitrocellulose Membranes The nucleic acid extracts of clinical samples L1, L2, L3, L4, L5, and L6, the 1 pg/μl plasmid solution of HPV type 16, and the 1 pg/μl salmon sperm DNA solution were each collected in a volume of 1 μl, spotted on each of the nitrocellulose membranes, and dried at room temperature.

The layout of the target DNA on the surface of each of the nitrocellulose membranes was shown in Table 4 below.

TABLE 4

| L1 | L2 | L3 | Positive control |
| L4 | L5 | L6 | Positive control |

2.2.3 Denaturation

The nitrocellulose membranes were soaked in the denaturing solution for 10 min, the purpose of which was to alter the double strand of the genome into single strands, and thus to facilitate hybridization with DNA probes in subsequent steps.

2.2.4 Neutralization

The denatured nitrocellulose membranes were soaked again into the 10×SSC buffer solution for 10 min.

2.2.5 Drying

The nitrocellulose membranes were taken out of the buffer solution, and excess water was absorbed therefrom with filter paper, followed by one-hour drying at 80° C.

Procedure 3 Pretreatment 3.1 Preparation of a Pretreatment Solution

The pretreatment solution included the components of 0.1 mol/L Tris-HCl having a pH value of 8.0, 1 mol/L NaCl, 2% BSA, 0.3% TWEEN-20 (Polysorbate-20), 0.15% SLS, 0.2% APAM, and water as a balance.

3.2 Pretreatment

The nitrocellulose membranes immobilized with whole genome samples of HPV on the surfaces thereof, as obtained procedure 2, were soaked in the pretreatment solution at 37° C. for 30 min, during which, the nitrocellulose membranes were flipped once.

Procedure 4 Preliminary Treatment 4.1 Preparation of a Preliminary Treatment Solution The preliminary solution included the components of 0.1 mol/L Tris-HCl having a pH value of 7.5, 1 mol/L NaCl, and water as a balance.

4.2 Preliminary Treatment

The nitrocellulose membranes obtained after the pretreatment in procedure 3 were each treated on the surfaces thereof with the preliminary treatment solution three times, each time for 5 min.

Procedure 5 One-step Reaction 5.1 Experimental Materials

Sangon Biotech (Shanghai) Co., Ltd. was entrusted to synthesize 13 types of DNA probes, the 5' ends of which were biotin-labeled, for detecting HPV. The nucleotide sequences of the DNA probes were respectively shown in SEQ ID NOs: 35, 36, 37, 38, 39, 40, 41, 42, 43, 44, 45, 46, and 47. Sterile pure water was used to dissolve the dry powders of the above 13 types of probes, to prepare 50 pmol/ml probe solutions, respectively. The 13 HPV types were respectively HPV types 16, 18, 31, 33, 35, 39, 45, 51, 52, 56, 58, 59, and 68.

5.2 Preparation of a Hybridization Solution

The hybridization solution contained the components of the above 13 0.5 pmol/ml HPV DNA probes, 3×SSC, 20 ng/ml SA-AP, 10 mM ZnCl2, 10 mM MgCl2, 0.3% TWEEN-20 (Polysorbate-20), 0.04% SLS, 5% polyethylene glycol 8000, and water as a balance.

5.3 One-step Reaction

The nitrocellulose membranes, each immobilized with the samples to be tested, the positive control sample, and the negative control sample on the surfaces thereof, as treated in the above preliminary treatment in procedure 4, were placed in the above hybridization solution, followed by 10-minute reactions at 37° C. in water baths.

Procedure 6 Aftertreatment 6.1 Preparation of an Aftertreatment Solution

The aftertreatment solution included the components of 0.1 mol/L Tris-HCl having a pH value of 9.5, 0.1 mol/L NaCl, 1% n-dodecylglucoside, and water as a balance.

6.2 Aftertreatment

The nitrocellulose membranes, as obtained in the above one-step reaction in procedure 5, were washed with the aftertreatment solution three times, each time for 5 min.

Procedure 7 Color Development Reaction 7.1 Preparation of a Substrate Solution

The substrate solution included the following components: 0.1 mol/L Tris-HCl having a pH value of 10.0, 0.1 mol/L NaCl, 50 mM MgCl2, 0.33 mg/ml NBT, 0.17 mg/ml BCIP, and water as a balance.

7.2 Color Development Reaction

The nitrocellulose membranes, after being treated in the aftertreatment of procedure 6, were respectively soaked in the substrate solution for 5-10 minute color development. Color development results were then observed.

The color development results of this example were shown in Table 7.

COMPARATIVE EXAMPLE 1

The conditions and procedures were respectively the same as those in Example 1, except that the hybridization solution did not contain the cationic polymer, the zinc ions, or the magnesium ions, and that the color developing solution did not contain the alkylglucoside.

Figure 6:
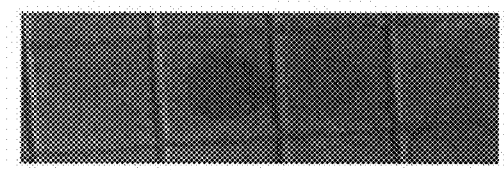
FIG. 6 shows a color development result of Comparative Example 1 of the present disclosure.

The color development results of this example were shown in FIG. 6 and Table 7.

COMPARATIVE EXAMPLE 2

Figure 7:
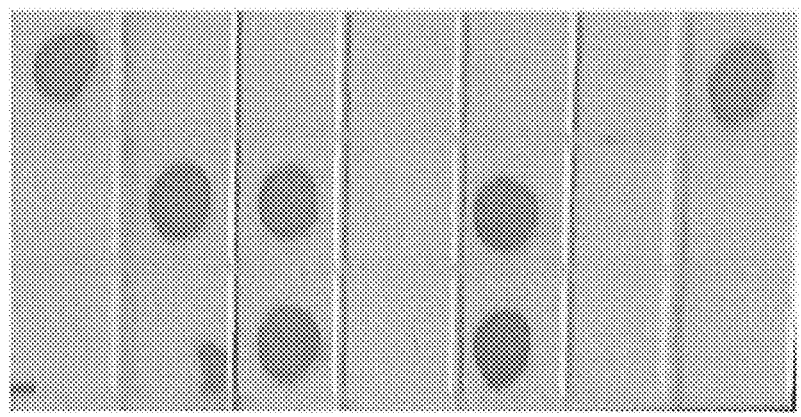
FIG. 7 shows a color development result of Comparative Example 2 of the present disclosure.

In this example, a comparative example of the present disclosure, Qiagen's "HCII high-risk HPV capture hybridization kit" was used to detect the six clinical samples of Example 35, which were obtained from cervical exfoliated cell preservation solutions of patients whose clinical cytology examination results were ASCUS or higher scale. These six samples were respectively labeled L1, L2, L3, L4, L5, and L6. The detection result (see FIG. 7) indicated that samples L1, L2, and L4 were positive, while samples L3, L5, and L6 were negative.

According to Example 35, the test kit used of the present disclosure can perform accurate detection on HPV in the clinical samples, among which, clinical sample L2 was strong positive, while clinical samples L1 and L4 were moderately strong positive. This indicated that clinical samples L1, L2, and L4 contained one or more high-risk HPV types selected from a group consisting of 13 different genotypes as shown in SEQ ID NOs: 35, 36, 37, 38, 39, 40, 41, 42, 43, 44, 45, 46, and 47. Clinical samples L3, L5, and L6 were detected to be negative. The target DNA did not show any nonspecific results in the detection of the clinical samples with the test kit of the present disclosure, which was completely consistent with the detection results of HCII in Comparative Example 2. The positive control (plasmid of HPV 16) was obviously positive, and the negative control (salmon sperm DNA) was negative. The results of quality control further indicated that, the test kit of the present disclosure was not only completely normal during the detection of the clinical samples, but also had very low color background of the solid support. This was helpful for the interpretation of the results, thereby improving specificity of the detection.

Results

Table 5 showed that the results of Examples 1 and 10 were significantly superior to those of Comparative Example 1. This indicated that the cationic polymer was capable of not only improving the sensitivity of chips, but also reducing background color (i.e., the color background became faded lighter). In addition, the result of Example 1 showed a faded background color as compared with the result of of Example 10, which was beneficial for interpretation of the results, and indicated that the alkylglucoside in the color developing solution could reduce the background color as well. The results of Examples 10, 2, and 3, in which CPAM, PLL, and polyaluminium chloride were respectively added, showed that the sensitivity of color development could be improved, as compared with the results of Comparative Example 1. The sensitivity of color development between and among Examples 10, 2 and 3, however, did not show any difference, indicating that the sensitivity of color development could be obviously improved through mere addition of any one of CPAM, PLL, and polyaluminium chloride into the hybridization solution. The results of Examples 4 and 5, with addition of zinc ions and magnesium ions respectively, showed improvement in sensitivity of color development, as compared with the results of Examples 1, 2, and 10. The results of Examples 4 and 5, however, did not show any significant difference regarding sensitivity of color development, indicating that both zinc ions and magnesium ions could improve the sensitivity of color development. The results of Examples 6 and 7, with addition of both zinc ions and magnesium ions, showed significant improvement in sensitivity, as compared with the results of Examples 4 and 5, and besides, the results of Example 7 showed improvement in specificity over the results of Example 6, indicating that when both zinc ions and magnesium ions were contained in the hybridization solution, the chip was most sensitive in color development. Compared with the results of Comparative Example 1, the results of Examples 8 and 9 showed both significantly improved sensitivity and faded color background. Compared with the results of Examples 8, in which dodecylglucoside is absent, the results of Example 9 showed significantly paler color background, which indicated that dodecylglucoside was more helpful in reducing the background than magnesium chloride. The above results showed that an optimum color effect can be achieved when zinc ions, magnesium ions, and any one of CPAM, PLL, and polyaluminium chloride were added in the hybridization solution, while dodecylglucoside and magnesium chloride were added in the color developing solution.

TABLE 5

| Example | Hybridization solution | | | | | | | Color developing solution Buffer solution (pH = 9.5) |
|---|---|---|---|---|---|---|---|---|
| | CPAM | PLL | Polyaluminum chloride | Zinc ion | Magnesium ion | BSA | Polyethylene glycol 8000 | |
| Example 1 | | 0.1% | None | None | None | None | None | ✓ |
| Example 2 | 0.5% | None | None | None | None | None | None | ✓ |
| Example 3 | None | None | 0.2% | None | None | None | None | ✓ |
| Example 4 | None | 0.1% | None | ✓ | None | None | None | ✓ |
| Example 5 | None | 0.1% | None | None | ✓ | None | None | ✓ |
| Example 6 | None | 0.1% | None | ✓ | ✓ | None | None | ✓ |
| Example 7 | None | 0.1% | None | ✓ | ✓ | ✓ | ✓ | ✓ |
| Example 8 | None | 0.1% | None | ✓ | ✓ | ✓ | ✓ | ✓ |
| Example 9 | None | 0.1% | None | ✓ | ✓ | ✓ | ✓ | ✓ |
| Example 10 | None | 0.1% | None | None | None | None | None | ✓ |
| Comparative Example 1 | | | | | None | | | |

| Example | Color developing solution | | | Color background | Sensitivity |
|---|---|---|---|---|---|
| | Magnesium ion (mM) | Alkylglucoside | Specificity | | |
| Example 1 | 50 | 0.07% | 0 | --- | ↑ |
| Example 2 | 50 | 0.07% | 0 | --- | ↑ |
| Example 3 | 50 | 0.07% | 0 | --- | ↑ |
| Example 4 | 50 | 0.07% | 0 | --- | ↑↑ |
| Example 5 | 50 | 0.07% | 0 | --- | ↑↑ |
| Example 6 | 50 | 0.07% | 0 | --- | ↑↑↑ |
| Example 7 | 50 | 0.07% | ↑ | --- | ↑↑↑ |
| Example 8 | None | None | ↑ | - | ↑↑↑ |
| Example 9 | None | 0.07% | ↑ | -- | ↑↑↑ |
| Example 10 | None | None | 0 | - | ↑ |
| Comparative Example 1 | | None | 0 | 0 | 0 |

Note:
the sign "✓" indicated existence of corresponding substances. Regarding "specificity," "sensitivity," and "color background," reference was made to Comparative Example 1, in which these items were all specified "0." Where the specificity and sensitivity obtained in the technical solutions of the examples were improved at different degrees, the signs "↑," "↑↑," "↑↑↑," . . . were used to represent such different degrees from small to large. Where the color background obtained in the technical solutions of the examples was decreased at different degrees, the signs "-," "--," "---," . . . were used to represent such different degrees from small to large. The paler the color background obtained, the better the color of the sample and that of the background could be distinguished from each other, and thus the better the results could be distinguished.

TABLE 6

| Example | Hybridization solution | | | | | | Color developing solution | | | Specificity | Color background | Sensitivity |
|---|---|---|---|---|---|---|---|---|---|---|---|---|
| | pH value of the buffer solution | SA-AP (µg/ml) | Non-ionic surfactant (v/v) | Cationic polymer (v/v) | Zinc ion (mol/L) | Magnesium ion (mol/L) | Buffer solution (pH = 9.5) | Magnesium ion (mM) | Alkylglucoside | | | |
| Example 11 | 6.5 | 0.05 | 0.01% | 0.01% | 0.001 | 0.001 | ✓ | 50 | 0.07% | ↑ | -- | ↑ |
| Example 12 | 8.5 | 2 | 2% | 0.2% | 0.1 | 0.1 | ✓ | 50 | 0.07% | ↑ | -- | ↑↑ |
| Example 13 | 7.0 | 1.2 | 1% | 0.2% | 0.05 | 0.05 | ✓ | 50 | 0.07% | ↑↑ | -- | ↑↑ |
| Example 14 | 7.0 | 1.2 | 1% | 0.2% | 0.05 | 0.05 | ✓ | 50 | 0.01% | ↑↑ | - | ↑↑ |
| Example 15 | 7.0 | 1.2 | 1% | 0.2% | 0.05 | 0.05 | ✓ | 50 | 0.5% | ↑↑ | - | ↑↑ |
| Example 16 | 7.0 | 1.2 | 1% | 0.2% | 0.05 | 0.05 | ✓ | 50 | 0.05% | ↑↑ | -- | ↑↑ |
| Example 17 | 7.0 | 1.2 | 1% | 0.2% | 0.05 | 0.05 | ✓ | 50 | 0.1% | ↑↑ | -- | ↑↑ |
| Example 1 | 7.0 | 1 | 0.5% | None | None | None | ✓ | None | None | 0 | 0 | 0 |

Notes:
the sign "✓" indicated existence of corresponding substances. Regarding "specificity," "sensitivity," and "color background," reference was made to Comparative Example 1, in which these items were all specified "0." Where the specificity and sensitivity obtained in the technical solutions of the examples were improved at different degrees, the signs "↑," "↑↑," "↑↑↑," . . . were used to represent such different degrees from small to large. Where the color background obtained in the technical solutions of the examples was decreased at different degrees, the signs "-," "--," "---," . . . were used to represent such different degrees from small to large. The paler the color background obtained, the better the color of the sample and that of the background could be distinguished from each other, and thus the better the results could be distinguished.

Table 6 indicated that the results of Examples 11, 12, and 13 were all significantly superior to the results of Comparative Example 1, and the results of Example 13 were superior to the results of Examples 11 and 12. In Example 11 to 13, the pH value of the hybridization buffer solution, and the concentrations of SA-AP, the non-ionic surfactant, the cationic polymer, the zinc ions, and the magnesium ions were in the ranges from 6.5 to 8.5, from 0.05 to 2 µg/ml, from 0.01% to 2%, from 0.01% to 0.2%, and from 0.001 to 0.1 mol/L, respectively. The pH value of the hybridization buffer solution, and the concentrations of SA-AP, the non-ionic surfactant, the cationic polymer, the zinc ions, and the magnesium ions in the technical solution of Example 13 were all preferred options. Among the results of Examples 13-17, the results of Example 13 showed a lightest color background and a highest sensitivity. That is, compared with the technical solutions of Examples 11, 12, and 14-17, the technical solution of Example 13 produced a better color result. As can be concluded, the concentrations of the cationic polymer, the zinc ions, the magnesium ions, and the alkylglucoside in Example 13 were all preferred options.

0.1%. The results of Examples 30 and 31 were significantly superior to the results of Comparative Example 1, but the results of Example 18 were superior to those of Examples 30 and 31, indicating that optimal effects could be achieved through simultaneous addition of magnesium ions and dodecylglucoside in the aftertreatment solution. The results of Examples 33, 34, and 35 showed obviously better specificity and color background than those indicated in the results of Comparative Example 1, and the sensitivity as indicated in

TABLE 7

| Example | Pretreatment solution Base solution | pH value of the buffer solution | SLS | ARAM | Preliminary treatment solution Base solution | pH value of the buffer solution | After treatment solution Base solution | Magnesium ion (mM) | Dedecyglucoside | Specificity | Color back-ground | Sensitivity |
|---|---|---|---|---|---|---|---|---|---|---|---|---|
| Example 18 | ✓ | 7.5 | 0.15% | 0.2% | ✓ | 7.5 | ✓ | 50 | 1% | ↑↑↑↑ | --- | ↑↑ |
| Example 19 | ✓ | 7.0 | 0.15% | 0.2% | ✓ | 7.0 | ✓ | 50 | 1% | ↑↑↑ | --- | ↑↑ |
| Example 20 | ✓ | 8.0 | 0.15% | 0.2% | ✓ | 9.0 | ✓ | 50 | 1% | ↑↑↑ | --- | ↑↑ |
| Example 21 | ✓ | 7.5 | 0.15% | 0.2% | ✓ | 7.5 | | None | | ↑↑↑ | - | ↑↑ |
| Example 22 | ✓ | 7.5 | None | None | ✓ | 7.5 | | None | | ↑ | - | 0 |
| Example 23 | ✓ | 7.5 | 0.05% | None | ✓ | 7.5 | | None | | ↑↑ | - | ↑ |
| Example 24 | ✓ | 7.5 | 2% | None | ✓ | 7.5 | | None | | ↑↑ | - | ↑ |
| Example 25 | ✓ | 7.5 | 0.1% | None | ✓ | 7.5 | | None | | ↑↑↑ | - | ↑ |
| Example 26 | ✓ | 7.5 | None | 0.05% | ✓ | 7.5 | | None | | ↑↑ | - | ↑ |
| Example 27 | ✓ | 7.5 | None | 0.1% | ✓ | 7.5 | | None | | ↑↑ | - | ↑ |
| Example 28 | ✓ | 7.5 | None | 0.15% | ✓ | 7.5 | | None | | ↑↑↑ | - | ↑ |
| Example 29 | | None | | | | None | ✓ | 50 | 1% | 0 | --- | 0 |
| Example 30 | ✓ | 7.5 | 0.15% | 0.2% | ✓ | 7.5 | ✓ | 50 | None | ↑↑↑↑ | -- | ↑↑ |
| Example 31 | ✓ | 7.5 | 0.15% | 0.2% | ✓ | 7.5 | ✓ | None | 1% | ↑↑↑↑ | -- | ↑↑ |
| Example 32 | ✓ | 7.5 | 0.15% | 0.2% | ✓ | 7.5 | ✓ | None | None | ↑↑↑↑ | - | ↑↑ |
| Example 33 | ✓ | 7.5 | 0.15% | 0.2% | ✓ | 7.5 | ✓ | 50 | 1% | ↑↑↑↑ | --- | ↑↑ |
| Example 34 | ✓ | 7.5 | 0.15% | 0.2% | ✓ | 7.5 | ✓ | 50 | 1% | ↑↑↑↑ | --- | ↑↑↑ |
| Example 35 | ✓ | 7.5 | 0.15% | 0.2% | ✓ | 7.5 | ✓ | 50 | 1% | ↑↑↑↑ | --- | 0 |
| Comparative Example 1 | | | | | | None | | | | 0 | 0 | 0 |

Notes:
the sign "✓" indicated existence of corresponding substances. Regarding "specificity," and "color background," reference was made to Comparative Example 1, in which these items were all specified "0." Where the specificity obtained in the technical solutions of the examples were improved at different degrees, the signs "↑," "↑↑," "↑↑↑," ... were used to represent such different degrees from small to large. Where the color background obtained in the technical solutions of the examples was decreased at different degrees, the signs "-," "--," "---," ... were used to represent such different degrees from small to large. The paler the color background obtained, the better the color of the sample and that of the background could be distinguished from each other, and thus the better the results could be distinguished.

Table 7 showed that the results of Examples 18, 19, 20, and 21 were significantly superior to the results of Comparative Example 1, indicating that relatively favorable experimental results could be obtained when the pH value of the pretreatment solution was in the range from 7.0 to 8.0, and the pH value of the preliminary treatment solution was in the range from 7.0 to 9.0. Example 18 showed better specificity than both Examples 19 and 20, indicating that the pH value of the pretreatment solution and that of the preliminary treatment solution used in Example 18, both being 7.5, were preferred options. And compared with the results of Example 21, the results of Example 18 showed relatively pale background color, which was favorable for judgment of the results, indicating that the magnesium ions and dodecylglucoside could reduce the background color. The results of Examples 22-28 showed better specificity and background respectively than those indicated in the results of Comparative Example 1. The results of Example 25 were superior to those of Examples 23 and 24, indicating that the concentration of sodium lignosulfonate could vary in the range from 0.05% to 0.2%, preferably being 0.1%. The results of Example 27 were superior to those of Examples 26 and 28, indicating that the concentration of APAM could vary in the range from 0.05% to 0.15%, preferably being 0.1%. The results of Examples 30 and 31 were significantly superior to the results of Comparative Example 1, but the results of Example 18 were superior to those of Examples 30 and 31, indicating that optimal effects could be achieved through simultaneous addition of magnesium ions and dodecylglucoside in the aftertreatment solution. The results of Examples 33, 34, and 35 showed obviously better specificity and color background than those indicated in the results of Comparative Example 1, and the sensitivity as indicated in the results of Example 34 was better than that as indicated in the results of Example 33. It could thus be proved, in the technical solution of Example 34, the pH value of the pretreatment solution, the concentrations of sodium lignosulfonate and APAM in the pretreatment solution, the pH value of the preliminary treatment solution, and the concentration of dodecylglucoside in the aftertreatment solution were all preferred options.

To conclude the above, SA-AP and HPV DNA probes were directly included in the hybridization solution of the test kit, such that during molecular hybridization between the target DNA and the biotin-labeled DNA probe on the surface of the solid support, SA-AP and biotin were simultaneously bound to each other. Meanwhile, the pretreatment solution, the preliminary treatment solution, and the aftertreatment solution were used to cooperatively treat the surface of the solid support before and after the one-step reaction. As a result, not only a separate ELISA, which would be necessary after molecular hybridization in the prior art, could be omitted, thereby significantly improving detection efficiency of the target DNA in the sample, but the positive detection results were rather distinct against extremely low detection background as well. In fact, at each spot where the target DNA was located, except for the DNA probe of a corresponding type, none of other types of DNA probes would be colored. As can be seen, the detection of the test kit had obvious characteristics of high specificity and low background, thereby effectively preventing a false positive test result.

It should be noted that the above examples are only used to explain, rather than to limit the present disclosure in any manner. Although the present disclosure has been discussed with reference to typical examples, it should be understood that the terms and expressions adopted are for describing and explaining instead of limiting the present disclosure. The present disclosure can be modified within the scope of the claims, or can be amended without departing from the scope or spirits thereof. Although the present disclosure is described with specific methods, materials, and examples, the scope of the present disclosure herein disclosed should not be limited by the particularly disclosed examples as described above, but can be extended to other methods and use having the same functions.

The invention claimed is:

1. A test kit for detecting a target nucleic acid in a sample, comprising a hybridization solution, a pretreatment solution and a preliminary treatment solution therein,
wherein the hybridization solution contains therein a non-ionic surfactant, a cationic polymer, and a buffer solution having a pH value in the range from 6.5 to 8.5,
wherein the cationic polymer is at least one selected from a group consisting of cationic polyacrylamide and polyaluminium chloride,
wherein in the hybridization solution, the ratio of the weight of the cationic polymer to the volume of the non-ionic surfactant is (1-4): (1-20),
wherein the pretreatment solution contains a Tris-HCl buffer solution having a pH value in the range from 7.0 to 8.0, NaCl, a sealant, a non-ionic surfactant, an anionic dispersant and/or anionic polyacrylamide, the weight ratio of the anionic dispersant to Tris being (10-15):121, and the anionic dispersant being selected from lignosulphonates,
wherein the preliminary treatment solution contains NaCl and a buffer solution having a pH value in the range from 7.0 to 9.0, which is selected from a group consisting of barbital sodium-hydrochloric acid buffer solution, Tris-HCl buffer solution, glycine-sodium hydroxide buffer solution, and boric acid-borax buffer solution, and
the test kit further comprises therein a Tris-HCl color developing solution having a pH value in the range from 9.0 to 10.0, wherein the color developing solution contains therein a C8-C18 alkylglucoside, and the weight ratio of the alkylglucoside to Tris is (5-10): 121,
wherein the sealant is bovine serum albumin, and the non-ionic surfactant is TWEEN-20 (Polysorbate-20).

2. The test kit according to claim 1, wherein the hybridization solution further contains zinc ions and/or magnesium ions,
wherein the weight ratio of the zinc ions to the cationic polymer is (13-130): (20-80), and
wherein the weight ratio of the magnesium ions to the cationic polymer is (12-120): (25-100).

3. The test kit according to claim 1, wherein the hybridization solution further contains therein alkaline phosphatase labeled-streptavidin, and
wherein the weight ratio of the alkaline phosphatase labeled-streptavidin to the cationic polymer is (5-12): (5000-20,000).

4. The test kit according to claim 1, wherein the hybridization solution further contains therein a protein, which is at least one selected from a group consisting of albumin, casein, and gelatin, and
wherein the weight ratio of the protein to the cationic polymer is (20-100): (1-4).

5. The test kit according to claim 1, wherein the pH value of the buffer solution contained in the hybridization solution is in the range from 6.8 to 7.2; and/or
wherein the pH value of the color developing solution is in the range from 9.3 to 9.7.

6. The test kit according to claim 1,
wherein in the pretreatment solution, the weight ratio of the sealant to Tris is (200-400):121, and
wherein in the pretreatment solution, the weight ratio of the non-ionic surfactant to Tris is (5-20):121.

7. The test kit according to claim 1, wherein the anionic dispersant is sodium lignosulphonate.

8. The test kit according to claim 1, wherein the test kit further contains therein an aftertreatment solution, which contains therein a buffer solution having a pH value in the range from 9.0 to 10.0, which is selected from a group consisting of barbital sodium-hydrochloric acid buffer solution, Tris-HCl buffer solution, glycine-sodium hydroxide buffer solution, and boric acid-borax buffer solution,
wherein the aftertreatment solution further contains therein magnesium ions and/or a $C_8$-$C_{18}$ alkylglucoside, and
wherein the weight ratio of the alkylglucoside to Tris is (50-200):121.

* * * * *

SEQUENCE LISTING

```
<160> NUMBER OF SEQ ID NOS: 49

<210> SEQ ID NO 1
<211> LENGTH: 18
<212> TYPE: DNA
<213> ORGANISM: Artificial sequence
<220> FEATURE:
<223> OTHER INFORMATION: an oligonucleotide probe for detecting mutation
      in the rpoB gene of Mycobacterium tuberculosisat at codon 533

<400> SEQUENCE: 1
ggccgcagcg ccgacagt                                                 18

<210> SEQ ID NO 2
<211> LENGTH: 18
<212> TYPE: DNA
<213> ORGANISM: Artificial sequence
<220> FEATURE:
<223> OTHER INFORMATION: an oligonucleotide probe for detecting T533C
      mutant of the rpoB gene of Mycobacterium tuberculosis

<400> SEQUENCE: 2
ggcgccggcg ccgacagt                                                 18

<210> SEQ ID NO 3
<211> LENGTH: 20
<212> TYPE: DNA
<213> ORGANISM: Artificial sequence
<220> FEATURE:
<223> OTHER INFORMATION: a positive control probe

<400> SEQUENCE: 3
gatggcaagg gacttcctgt                                               20

<210> SEQ ID NO 4
<211> LENGTH: 22
<212> TYPE: DNA
<213> ORGANISM: Artificial sequence
<220> FEATURE:
<223> OTHER INFORMATION: a negative control probe

<400> SEQUENCE: 4
tcctgaggag aagtctgccg tt                                            22

<210> SEQ ID NO 5
<211> LENGTH: 19
<212> TYPE: DNA
<213> ORGANISM: Artificial sequence
<220> FEATURE:
<223> OTHER INFORMATION: an upstream primer for amplification of the
      rpoB gene of Mycobacterium tuberculosis

<400> SEQUENCE: 5
ggtggtcgcc gcgatcaag                                                19
```

```
<210> SEQ ID NO 6
<211> LENGTH: 20
<212> TYPE: DNA
<213> ORGANISM: Artificial sequence
<220> FEATURE:
<223> OTHER INFORMATION: a downstream primer for amplification of the
      rpoB gene of Mycobacterium tuberculosis

<400> SEQUENCE: 6
cgagccgatc agaccgatgt                                              20

<210> SEQ ID NO 7
<211> LENGTH: 19
<212> TYPE: DNA
<213> ORGANISM: Artificial sequence
<220> FEATURE:
<223> OTHER INFORMATION: an upstream primer for amplification of a human
      actin gene

<400> SEQUENCE: 7
gcgagcatcc cccaaagtt                                               19

<210> SEQ ID NO 8
<211> LENGTH: 19
<212> TYPE: DNA
<213> ORGANISM: Artificial sequence
<220> FEATURE:
<223> OTHER INFORMATION: a downstream primer for amplification of a
      human actin gene

<400> SEQUENCE: 8
ggcacgaagg ctcatcatt                                               19

<210> SEQ ID NO 9
<211> LENGTH: 18
<212> TYPE: DNA
<213> ORGANISM: Artificial sequence
<220> FEATURE:
<223> OTHER INFORMATION: HPV16-probe

<400> SEQUENCE: 9
ttctgaagta gatatggc                                                18

<210> SEQ ID NO 10
<211> LENGTH: 17
<212> TYPE: DNA
<213> ORGANISM: Artificial sequence
<220> FEATURE:
<223> OTHER INFORMATION: HPV18-probe

<400> SEQUENCE: 10
ttgcccaggt acaggag                                                 17

<210> SEQ ID NO 11
<211> LENGTH: 17
<212> TYPE: DNA
<213> ORGANISM: Artificial sequence
<220> FEATURE:
<223> OTHER INFORMATION: HPV6-probe

<400> SEQUENCE: 11
gaagatgtag ttacgga                                                 17

<210> SEQ ID NO 12
<211> LENGTH: 17
<212> TYPE: DNA
<213> ORGANISM: Artificial sequence
```

```
<220> FEATURE:
<223> OTHER INFORMATION: HPV11-probe

<400> SEQUENCE: 12
gtagcagatt tagacac                                              17

<210> SEQ ID NO 13
<211> LENGTH: 19
<212> TYPE: DNA
<213> ORGANISM: Artificial sequence
<220> FEATURE:
<223> OTHER INFORMATION: an oligonucleotide probe for detecting
      Mycobacterium tuberculosis

<400> SEQUENCE: 13
aagacatgca tcccgtggt                                            19

<210> SEQ ID NO 14
<211> LENGTH: 20
<212> TYPE: DNA
<213> ORGANISM: Artificial sequence
<220> FEATURE:
<223> OTHER INFORMATION: an oligonucleotide probe for detecting
      Mycobacterium avium

<400> SEQUENCE: 14
gaagacatgc gtcttgaggt                                           20

<210> SEQ ID NO 15
<211> LENGTH: 20
<212> TYPE: DNA
<213> ORGANISM: Artificial sequence
<220> FEATURE:
<223> OTHER INFORMATION: an oligonucleotide probe for detecting a
      Mycobacterium intracellular

<400> SEQUENCE: 15
ctaaagacat gcgcctaaag                                           20

<210> SEQ ID NO 16
<211> LENGTH: 19
<212> TYPE: DNA
<213> ORGANISM: Artificial sequence
<220> FEATURE:
<223> OTHER INFORMATION: an oligonucleotide probe for detecting
      Mycobacterium fortuitum

<400> SEQUENCE: 16
cacacaccat gaagcgcgt                                            19

<210> SEQ ID NO 17
<211> LENGTH: 19
<212> TYPE: DNA
<213> ORGANISM: Artificial sequence
<220> FEATURE:
<223> OTHER INFORMATION: an oligonucleotide probe for detecting
      Mycobacterium abscessus

<400> SEQUENCE: 17
ccactcacca tgaagtgtg                                            19

<210> SEQ ID NO 18
<211> LENGTH: 19
<212> TYPE: DNA
<213> ORGANISM: Artificial sequence
<220> FEATURE:
<223> OTHER INFORMATION: an oligonucleotide probe for detecting
```

Mycobacterium kansasii

<400> SEQUENCE: 18
aggcatgcgc caagtggtc                                                    19

<210> SEQ ID NO 19
<211> LENGTH: 18
<212> TYPE: DNA
<213> ORGANISM: Artificial sequence
<220> FEATURE:
<223> OTHER INFORMATION: an oligonucleotide probe for detecting T533C
      wild type of the rpoB gene of Mycobacterium tuberculosis

<400> SEQUENCE: 19
ggccgcagcg ccgacagt                                                     18

<210> SEQ ID NO 20
<211> LENGTH: 20
<212> TYPE: DNA
<213> ORGANISM: Artificial sequence
<220> FEATURE:
<223> OTHER INFORMATION: an oligonucleotide probe for detecting C531T
      wild type of the rpoB gene of Mycobacterium tuberculosi

<400> SEQUENCE: 20
ccagggccga cagtcggcgc                                                   20

<210> SEQ ID NO 21
<211> LENGTH: 20
<212> TYPE: DNA
<213> ORGANISM: Artificial sequence
<220> FEATURE:
<223> OTHER INFORMATION: an oligonucleotide probe for detecting C531T
      mutant of the rpoB gene of Mycobacterium tuberculosis

<400> SEQUENCE: 21
ccagggccaa cagtcggcgc                                                   20

<210> SEQ ID NO 22
<211> LENGTH: 19
<212> TYPE: DNA
<213> ORGANISM: Artificial sequence
<220> FEATURE:
<223> OTHER INFORMATION: an oligonucleotide probe for detecting 526 wild
      type of the rpoB gene of Mycobacterium tuberculosis

<400> SEQUENCE: 22
cggcgcttgt gggtgaacc                                                    19

<210> SEQ ID NO 23
<211> LENGTH: 19
<212> TYPE: DNA
<213> ORGANISM: Artificial sequence
<220> FEATURE:
<223> OTHER INFORMATION: an oligonucleotide probe for detecting C526G
      mutant of the rpoB gene of Mycobacterium tuberculosis

<400> SEQUENCE: 23
cggcgcttgt cggtgaacc                                                    19

<210> SEQ ID NO 24
<211> LENGTH: 18
<212> TYPE: DNA
<213> ORGANISM: Artificial sequence
<220> FEATURE:
<223> OTHER INFORMATION: an oligonucleotide probe for detecting C526T
      mutant of the rpoB gene of Mycobacterium tuberculosis

```
<400> SEQUENCE: 24
cggcgcttgt aggtgaac                                                 18

<210> SEQ ID NO 25
<211> LENGTH: 19
<212> TYPE: DNA
<213> ORGANISM: Artificial sequence
<220> FEATURE:
<223> OTHER INFORMATION: an oligonucleotide probe for detecting A526T
      mutant of the rpoB gene of Mycobacterium tuberculosis

<400> SEQUENCE: 25
cggcgcttga ggctcaacc                                                19

<210> SEQ ID NO 26
<211> LENGTH: 19
<212> TYPE: DNA
<213> ORGANISM: Artificial sequence
<220> FEATURE:
<223> OTHER INFORMATION: an oligonucleotide probe for detecting A526G
      mutant of the rpoB gene of Mycobacterium tuberculosis

<400> SEQUENCE: 26
cggcgcttgc ggctcaacc                                                19

<210> SEQ ID NO 27
<211> LENGTH: 20
<212> TYPE: DNA
<213> ORGANISM: Artificial sequence
<220> FEATURE:
<223> OTHER INFORMATION: an oligonucleotide probe for detecting A516T
      wild type of the rpoB gene of Mycobacterium tuberculosis

<400> SEQUENCE: 27
ttgttgtggt ccatgaattg                                               20

<210> SEQ ID NO 28
<211> LENGTH: 20
<212> TYPE: DNA
<213> ORGANISM: Artificial sequence
<220> FEATURE:
<223> OTHER INFORMATION: an oligonucleotide probe for detecting A516T
      mutant of the rpoB gene of Mycobacterium tuberculosis

<400> SEQUENCE: 28
ttgttgtgga ccatgaattg                                               20

<210> SEQ ID NO 29
<211> LENGTH: 18
<212> TYPE: DNA
<213> ORGANISM: Artificial sequence
<220> FEATURE:
<223> OTHER INFORMATION: an oligonucleotide probe for detecting T511C
      wild type of the rpoB gene of Mycobacterium tuberculosis

<400> SEQUENCE: 29
gaattggctc agctcgct                                                 18

<210> SEQ ID NO 30
<211> LENGTH: 19
<212> TYPE: DNA
<213> ORGANISM: Artificial sequence
<220> FEATURE:
<223> OTHER INFORMATION: an oligonucleotide probe for detecting T511C
      mutant of the rpoB gene of Mycobacterium tuberculosis
```

```
<400> SEQUENCE: 30
gaattggctc ggctcgctg                                                19

<210> SEQ ID NO 31
<211> LENGTH: 16
<212> TYPE: DNA
<213> ORGANISM: Artificial sequence
<220> FEATURE:
<223> OTHER INFORMATION: an upstream primer for amplification of the 16S
      rDNA gene

<400> SEQUENCE: 31
tggctcagga cgaacg                                                   16

<210> SEQ ID NO 32
<211> LENGTH: 18
<212> TYPE: DNA
<213> ORGANISM: Artificial sequence
<220> FEATURE:
<223> OTHER INFORMATION: a downstream primer for amplification of the
      16S rDNA gene

<400> SEQUENCE: 32
ggcttgcgcc cattgtgc                                                 18

<210> SEQ ID NO 33
<211> LENGTH: 39
<212> TYPE: DNA
<213> ORGANISM: Artificial sequence
<220> FEATURE:
<223> OTHER INFORMATION: an upstream primer for amplification of the
      rpoB gene

<400> SEQUENCE: 33
tcactcagca gactcagtca ggtggtcgcc gcgatcaag                          39

<210> SEQ ID NO 34
<211> LENGTH: 40
<212> TYPE: DNA
<213> ORGANISM: Artificial sequence
<220> FEATURE:
<223> OTHER INFORMATION: a downstream primer for amplification of the
      rpoB gene

<400> SEQUENCE: 34
aagagcctac cagtgatcgt cgagccgatc agaccgatgt                         40

<210> SEQ ID NO 35
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 16

<400> SEQUENCE: 35
atgtgctgcc atatctac                                                 18

<210> SEQ ID NO 36
<211> LENGTH: 17
<212> TYPE: DNA
<213> ORGANISM: Artificial sequence
<220> FEATURE:
<223> OTHER INFORMATION: an oligonucleotide probe for detecting HPV
      genotype 18

<400> SEQUENCE: 36
```

```
ctacacagtc tcctgta                                              17

<210> SEQ ID NO 37
<211> LENGTH: 20
<212> TYPE: DNA
<213> ORGANISM: Artificial sequence
<220> FEATURE:
<223> OTHER INFORMATION: an oligonucleotide probe for detecting HPV
      genotype 31

<400> SEQUENCE: 37
gctgcaattg caaacagtga                                           20

<210> SEQ ID NO 38
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 33

<400> SEQUENCE: 38
cacaagtaac tagtgaca                                             18

<210> SEQ ID NO 39
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 35

<400> SEQUENCE: 39
gtctgtgtgt tctgctgt                                             18

<210> SEQ ID NO 40
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 39

<400> SEQUENCE: 40
acctctatag agtcttcc                                             18

<210> SEQ ID NO 41
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 45

<400> SEQUENCE: 41
aatcctgtgc carrtaca                                             18

<210> SEQ ID NO 42
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 51

<400> SEQUENCE: 42
```

```
ctattagcac tgccactg                                             18

<210> SEQ ID NO 43
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 52

<400> SEQUENCE: 43
gactttatgt gctgargt                                             18

<210> SEQ ID NO 44
<211> LENGTH: 19
<212> TYPE: DNA
<213> ORGANISM: Artificial sequence
<220> FEATURE:
<223> OTHER INFORMATION: an oligonucleotide probe for detecting HPV
      genotype 56

<400> SEQUENCE: 44
gactattagt actgctaca                                            19

<210> SEQ ID NO 45
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 58

<400> SEQUENCE: 45
gacattatgc actgaagt                                             18

<210> SEQ ID NO 46
<211> LENGTH: 19
<212> TYPE: DNA
<213> ORGANISM: Artificial sequence
<220> FEATURE:
<223> OTHER INFORMATION: an oligonucleotide probe for detecting HPV
      genotype 59

<400> SEQUENCE: 46
gtgtgcttct actactkct                                            19

<210> SEQ ID NO 47
<211> LENGTH: 18
<212> TYPE: DNA
<213> ORGANISM: Artificial sequence
<220> FEATURE:
<223> OTHER INFORMATION: an oligonucleotide probe for detecting HPV
      genotype 68

<400> SEQUENCE: 47
ctactacaga ctctactg                                             18

<210> SEQ ID NO 48
<211> LENGTH: 20
<212> TYPE: DNA
<213> ORGANISM: Artificial sequence
<220> FEATURE:
<223> OTHER INFORMATION: an upstream primer of the enhanced primer pair

<400> SEQUENCE: 48
tcactcagca gactcagtca                                           20
```

```
<210> SEQ ID NO 49
<211> LENGTH: 20
<212> TYPE: DNA
<213> ORGANISM: Artificial sequence
<220> FEATURE:
<223> OTHER INFORMATION: a downstream primer of the enhanced primer pair

<400> SEQUENCE: 49
aagagcctac cagtgatcgt                                              20
```